United States Patent
Zhu et al.

(10) Patent No.: US 12,384,853 B2
(45) Date of Patent: Aug. 12, 2025

(54) ANTI-HER2/PD1 BISPECIFIC ANTIBODY

(71) Applicant: SUNSHINE GUOJIAN PHARMACEUTICAL (SHANGHAI) CO., LTD., Shanghai (CN)

(72) Inventors: Zhenping Zhu, Shanghai (CN); Haomin Huang, Shanghai (CN); Changling Gu, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 653 days.

(21) Appl. No.: 17/295,391

(22) PCT Filed: Oct. 22, 2019

(86) PCT No.: PCT/CN2019/112467
§ 371 (c)(1),
(2) Date: May 19, 2021

(87) PCT Pub. No.: WO2020/103629
PCT Pub. Date: May 28, 2020

(65) Prior Publication Data
US 2023/0287139 A1    Sep. 14, 2023

(30) Foreign Application Priority Data
Nov. 19, 2018 (CN) .......................... 201811376950.9

(51) Int. Cl.
| | |
|---|---|
| *C07K 16/00* | (2006.01) |
| *A61P 35/00* | (2006.01) |
| *C07K 16/28* | (2006.01) |
| *C07K 16/32* | (2006.01) |
| *A61K 39/00* | (2006.01) |

(52) U.S. Cl.
CPC .............. *C07K 16/32* (2013.01); *A61P 35/00* (2018.01); *C07K 16/2818* (2013.01); *A61K 2039/505* (2013.01); *C07K 2317/31* (2013.01); *C07K 2317/565* (2013.01); *C07K 2317/622* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2019/0367633 A1 | 12/2019 | Liu et al. | |
| 2020/0377597 A1* | 12/2020 | Zhao | ....................... A61P 37/06 |

FOREIGN PATENT DOCUMENTS

| | | |
|---|---|---|
| CN | 108341871 A | 7/2018 |
| WO | 9957134 | 11/1999 |
| WO | 2014052713 A2 | 4/2014 |
| WO | 20170136562 A2 | 8/2017 |

* cited by examiner

*Primary Examiner* — Meera Natarajan
(74) *Attorney, Agent, or Firm* — Gregory P. Einhorn; Greer, Burns & Crain., Ltd.

(57) ABSTRACT

Provided are an anti-HER2/PD1 bispecific antibody, preparation method, and antitumor application. Specifically, a single-chain variable fragment scFv and an immunoglobulin antibody IgG are connected by means of a peptide linker to obtain a bispecific antibody; the bispecific antibody can simultaneously target the tumor cell surface molecule HER2 antigen and T lymphocyte surface molecule PD-1. The results of experimentation show that the bispecific antibody provided is capable of inhibiting the proliferation of HER2-positive tumor cells while also blockading the binding of PD-1/PD-L1, releasing the suppressive state of T cells and performing an antitumor function.

10 Claims, 13 Drawing Sheets
Specification includes a Sequence Listing.

SEQUENCE LISTING

<160> NUMBER OF SEQ ID NOS: 26

<210> SEQ ID NO 1

```
<211> LENGTH: 5
<212> TYPE: PRT
<213> ORGANISM: Unknown
<220> FEATURE:
<223> OTHER INFORMATION: HCDR1

<400> SEQUENCE: 1

Ser Tyr Asp Met Ser
1               5

<210> SEQ ID NO 2
<211> LENGTH: 16
<212> TYPE: PRT
<213> ORGANISM: Unknown
<220> FEATURE:
<223> OTHER INFORMATION: HCDR2

<400> SEQUENCE: 2

Thr Ile Ser Gly Gly Gly Arg Tyr Thr Tyr Tyr Pro Asp Thr Val Lys
1               5                   10                  15

<210> SEQ ID NO 3
<211> LENGTH: 8
<212> TYPE: PRT
<213> ORGANISM: Unknown
<220> FEATURE:
<223> OTHER INFORMATION: HCDR3

<400> SEQUENCE: 3

Pro Tyr Gly Gly Tyr Phe Asp Val
1               5

<210> SEQ ID NO 4
<211> LENGTH: 11
<212> TYPE: PRT
<213> ORGANISM: Unknown
<220> FEATURE:
<223> OTHER INFORMATION: LCDR1

<400> SEQUENCE: 4

Arg Ala Ser Gln Ser Ile Ser Asn Phe Leu His
1               5                   10

<210> SEQ ID NO 5
<211> LENGTH: 7
<212> TYPE: PRT
<213> ORGANISM: Unknown
<220> FEATURE:
<223> OTHER INFORMATION: LCDR2

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Unknown
<220> FEATURE:
<223> OTHER INFORMATION: LCDR3

<400> SEQUENCE: 6

Gln Gln Ser Asn Ser Trp Pro His Thr
1               5

<210> SEQ ID NO 7
<211> LENGTH: 10
```

```
<212> TYPE: PRT
<213> ORGANISM: Unknown
<220> FEATURE:
<223> OTHER INFORMATION: HCDR4

<400> SEQUENCE: 7

Gly Phe Asn Ile Lys Asp Thr Tyr Ile His
1               5                   10

<210> SEQ ID NO 8
<211> LENGTH: 17
<212> TYPE: PRT
<213> ORGANISM: Unknown
<220> FEATURE:
<223> OTHER INFORMATION: HCDR5

<400> SEQUENCE: 8

Arg Ile Tyr Pro Thr Asn Gly Tyr Thr Arg Tyr Ala Asp Ser Val Lys
1               5                   10                  15

Gly

<210> SEQ ID NO 9
<211> LENGTH: 11
<212> TYPE: PRT
<213> ORGANISM: Unknown
<220> FEATURE:
<223> OTHER INFORMATION: HCDR6

<400> SEQUENCE: 9

Trp Gly Gly Asp Gly Phe Tyr Ala Met Asp Tyr
1               5                   10

<210> SEQ ID NO 10
<211> LENGTH: 11
<212> TYPE: PRT
<213> ORGANISM: Unknown
<220> FEATURE:
<223> OTHER INFORMATION: LCDR4

<400> SEQUENCE: 10

Arg Ala Ser Gln Asp Val Asn Thr Ala Val Ala
1               5                   10

<210> SEQ ID NO 11
<211> LENGTH: 8
<212> TYPE: PRT
<213> ORGANISM: Unknown
<220> FEATURE:
<223> OTHER INFORMATION: LCDR5

<400> SEQUENCE: 11

Ser Ala Ser Phe Leu Tyr Ser Gly
1               5

<210> SEQ ID NO 12
<211> LENGTH: 9
<212> TYPE: PRT
<213> ORGANISM: Unknown
<220> FEATURE:
<223> OTHER INFORMATION: LCDR6

<400> SEQUENCE: 12

Gln Gln His Tyr Thr Thr Pro Pro Thr
1               5

<210> SEQ ID NO 13
```

```
<211> LENGTH: 117
<212> TYPE: PRT
<213> ORGANISM: Unknown
<220> FEATURE:
<223> OTHER INFORMATION: scFv-VH

<400> SEQUENCE: 13

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Thr Ile Ser Gly Gly Arg Tyr Thr Tyr Tyr Pro Asp Thr Val
    50                  55                  60

Lys Gly Arg Phe Thr Ile Ser Arg Asp Asn Ala Lys Asn Ser His Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Gly Tyr Phe Asp Val Trp Gly Gln Gly Thr Leu
            100                 105                 110

Val Thr Val Ser Ser
            115

<210> SEQ ID NO 14
<211> LENGTH: 107
<212> TYPE: PRT
<213> ORGANISM: Unknown
<220> FEATURE:
<223> OTHER INFORMATION: scFv-VL

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Phe
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro His
                85                  90                  95

Thr Phe Gly Gln Gly Thr Lys Val Glu Ile Lys
            100                 105

<210> SEQ ID NO 15
<211> LENGTH: 120
<212> TYPE: PRT
<213> ORGANISM: Unknown
<220> FEATURE:
<223> OTHER INFORMATION: VH

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 16
<211> LENGTH: 107
<212> TYPE: PRT
<213> ORGANISM: Unknown
<220> FEATURE:
<223> OTHER INFORMATION: VL

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                      55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
                100                 105

<210> SEQ ID NO 17
<211> LENGTH: 20
<212> TYPE: PRT
<213> ORGANISM: Artificial Sequence
<220> FEATURE:
<223> OTHER INFORMATION: L1

<400> SEQUENCE: 17

Gly Gly Gly Gly Ser Gly Gly Gly Ser Gly Gly Gly Gly Ser Gly
 1               5                  10                  15

Gly Gly Gly Ser
             20

<210> SEQ ID NO 18
<211> LENGTH: 15
<212> TYPE: PRT
<213> ORGANISM: Artificial Sequence
<220> FEATURE:
<223> OTHER INFORMATION: L2

<400> SEQUENCE: 18

Gly Gly Gly Gly Ser Gly Gly Gly Ser Gly Gly Gly Gly Ser
 1               5                  10                  15
```

-continued

```
<210> SEQ ID NO 19
<211> LENGTH: 244
<212> TYPE: PRT
<213> ORGANISM: Artificial Sequence
<220> FEATURE:
<223> OTHER INFORMATION: scFv1

<400> SEQUENCE: 19
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Phe
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro His
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Gly Gly Ser Glu
        115                 120                 125

Val Lys Leu Val Glu Ser Gly Gly Leu Val Gln Pro Gly Gly Ser
    130                 135                 140

Leu Arg Leu Ser Cys Ala Ala Ser Gly Phe Ala Phe Ser Ser Tyr Asp
145                 150                 155                 160

Met Ser Trp Val Arg Gln Ala Pro Gly Lys Arg Leu Glu Trp Val Ala
                165                 170                 175

Thr Ile Ser Gly Gly Gly Arg Tyr Thr Tyr Tyr Pro Asp Thr Val Lys
            180                 185                 190

Gly Arg Phe Thr Ile Ser Arg Asp Asn Ala Lys Asn Ser His Tyr Leu
        195                 200                 205

Gln Met Asn Ser Leu Arg Ala Glu Asp Thr Ala Val Tyr Phe Cys Ala
    210                 215                 220

Ser Pro Tyr Gly Gly Tyr Phe Asp Val Trp Gly Gln Gly Thr Leu Val
225                 230                 235                 240

Thr Val Ser Ser

```
<210> SEQ ID NO 20
<211> LENGTH: 709
<212> TYPE: PRT
<213> ORGANISM: Artificial Sequence
<220> FEATURE:
<223> OTHER INFORMATION: heavy chain

<400> SEQUENCE: 20
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr

```
            65                  70                  75                  80
Leu Gln Met Asn Ser Leu Arg Ala Glu Asp Thr Ala Val Tyr Tyr Cys
                    85                  90                  95
Ser Arg Trp Gly Gly Asp Gly Phe Tyr Ala Met Asp Tyr Trp Gly Gln
                100                 105                 110
Gly Thr Leu Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys Gly Gly Gly Gly Ser Gly Gly Gly Ser Gly Gly Gly Gly
            450                 455                 460
Ser Glu Ile Val Leu Thr Gln Ser Pro Ala Thr Leu Ser Leu Ser Pro
465                 470                 475                 480
Gly Glu Arg Ala Thr Leu Ser Cys Arg Ala Ser Gln Ser Ile Ser Asn
                485                 490                 495
```

```
Phe Leu His Trp Tyr Gln Gln Lys Pro Gly Gln Ala Pro Arg Leu Leu
                500                 505                 510

Ile Lys Tyr Ala Ser Gln Ser Ile Ser Gly Ile Pro Ala Arg Phe Ser
            515                 520                 525

Gly Ser Gly Ser Gly Thr Asp Phe Thr Leu Thr Ile Ser Ser Leu Glu
        530                 535                 540

Pro Glu Asp Phe Ala Val Tyr Phe Cys Gln Gln Ser Asn Ser Trp Pro
545                 550                 555                 560

His Thr Phe Gly Gln Gly Thr Lys Val Glu Ile Lys Gly Gly Gly Gly
                565                 570                 575

Ser Gly Gly Gly Gly Ser Gly Gly Gly Ser Gly Gly Gly Gly Ser
        580                 585                 590

Glu Val Lys Leu Val Glu Ser Gly Gly Gly Leu Val Gln Pro Gly Gly
                595                 600                 605

Ser Leu Arg Leu Ser Cys Ala Ala Ser Gly Phe Ala Phe Ser Ser Tyr
        610                 615                 620

Asp Met Ser Trp Val Arg Gln Ala Pro Gly Lys Arg Leu Glu Trp Val
625                 630                 635                 640

Ala Thr Ile Ser Gly Gly Gly Arg Tyr Thr Tyr Tyr Pro Asp Thr Val
                645                 650                 655

Lys Gly Arg Phe Thr Ile Ser Arg Asp Asn Ala Lys Asn Ser His Tyr
                660                 665                 670

Leu Gln Met Asn Ser Leu Arg Ala Glu Asp Thr Ala Val Tyr Phe Cys
            675                 680                 685

Ala Ser Pro Tyr Gly Gly Tyr Phe Asp Val Trp Gly Gln Gly Thr Leu
        690                 695                 700

Val Thr Val Ser Ser
705

<210> SEQ ID NO 21
<211> LENGTH: 214
<212> TYPE: PRT
<213> ORGANISM: Artificial Sequence
<220> FEATURE:
<223> OTHER INFORMATION: light chain

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 2127
<212> TYPE: DNA
<213> ORGANISM: Artificial Sequence
<220> FEATURE:
<223> OTHER INFORMATION: heavy chain

<400> SEQUENCE: 22

```
gaggtccaac tggtggagtc cggaggagga ctggtgcaac ccggcggatc cctccggctg      60
tcttgtgctg ctagcggctt taacatcaag gataccttata tccattgggt taggcaagct     120
cccggtaagg gcttagaatg ggtcgctagg atctacccca ccaatggcta tactcgttac     180
gccgacagcg tgaagggtcg gttcaccatc tccgctgaca cctccaagaa cacagcttac     240
ctccaaatga actctttacg ggccgaggac acagccgtgt actactgttc ccggtgggga     300
ggcgacggct tctatgctat ggattactgg ggccaaggta cttttagtga cagtgtccagc   360
gccagcacaa aaggaccttc cgtcttccct ctggctccct cctccaagag caccagcggc     420
ggaacagctg ctctcggctg tctggtgaag gactacttcc ccgaacccgt accgtgtct    480
tggaattccg gcgctttaac ctccggcgtg cacacctttc cgctgttttt acagagcagc     540
ggcctctatt ctttaagctc cgtggtcaca gtgcctagca gctcttagg cacccagacc     600
tacatctgca acgtgaacca taagcccagc aataccaagg tcgacaagaa ggtggagccc     660
aagagctgcg ataagaccca cacatgtcct ccttgtcccg ctcccgaact gctgggagga     720
cccagcgtgt tttattcccc cccaaaaccc aaagacaccc tcatgatcag ccggacccccc    780
gaggtcacat gcgtggtggt ggacgtctcc cacgaagacc ccgaagtcaa gttcaactgg     840
tacgtggacg gagtcgaggt gcataacgcc aagacaaaac cccgggagga gcaatacaac     900
tccacctatc gtgtggtgag cgtgctcacc gtgctgcatc aagattggct gaatggcaag     960
gagtacaagt gcaaggtcag caacaaggct ctgcccgctc ctatcgagaa gacaatcagc    1020
aaagccaaag ccaacccccg ggagccccaa gtgtatactt tacccccctc ccgggaagag    1080
atgaccaaga accaagtttc tttaacatgt ttagtgaaag ctttttaccc ctccgacatc    1140
gccgtcgagt gggagtccaa tggccagccc gaaaataact acaagacaac ccccccgtg    1200
ctcgattccg atggatcctt cttttttatac agcaagctca cagtggataa gtcccggtgg    1260
cagcaaggaa acgtgttttc ttgttccgtc atgcacgagg ccctccataa ccactacacc     1320
cagaaatccc tctctctcag ccccggtaaa ggcggaggag gatccggcgg cggcggaagc    1380
ggaggaggcg gctccgagat cgtgctgacc cagtcccccg ctacactgtc cctctctccc    1440
ggtgaacggg ctactttaag ctgtcgtgcc agcaaagca tcagcaactt tttacactgg     1500
taccaacaga aacccggcca agctccccgg ctgctgatca gtacgcttc ccagagcatc     1560
agcggcattc ccgctaggt ctccggcagc ggcagcggaa ccgatttcac tttaaccatc     1620
```

```
agctctttag agcccgagga cttcgccgtc tacttctgcc aacagagcaa tagctggcct    1680
cacacattcg gccaaggtac aaaggtcgag atcaaaggtg gaggtggcag cggtggcggc    1740
ggcagcggtg gtggtggaag cggaggcgga ggctccgagg tgaagctcgt ggaatctggc    1800
ggaggtttag tgcagcccgg tggctcttta aggctgagct gtgctgccag cggctttgcc    1860
tttagctcct acgacatgag ctgggtgcgt caagctcccg aaagaggct ggagtgggtg    1920 gccacaatct ccggcggtgg tcgttatacc tattaccccg acaccgtcaa aggcggtttt    1980
accatcagcc gggacaacgc taagaacagc cattacctcc agatgaattc tttacgggct    2040
gaggacaccg ctgtgtattt ctgtgctagc ccctacggcg gctactttga tgtctgggga    2100
caaggtaccc tcgtgaccgt gagctcc                                       2127
```

<210> SEQ ID NO 23
<211> LENGTH: 642
<212> TYPE: DNA
<213> ORGANISM: Artificial Sequence
<220> FEATURE:
<223> OTHER INFORMATION: light chain

<400> SEQUENCE: 23

```
gacatccaga tgacacagag ccctcctct ttatccgctt ccgtgggaga tcgtgtcacc     60
atcacttgtc gtgcctccca agatgtgaac accgctgtgg cttggtacca gcagaagccc    120
ggtaaggctc ccaagctgct gatctactcc gccagctttt atactccgg cgtgccctct     180 cgtttctccg gatctcgttc cggcaccgac ttcactttaa ccatcagctc tttacagccc    240
gaggacttcg ccacctacta ctgccagcag cactacacca ccccccctac cttcggacaa    300
ggtaccaagg tggagatcaa gaggaccgtg gccgccccct ccgtcttcat ctttcccct    360 tccgacgagc agctgaagtc cggcacagcc tccgtggtgt gtttactgaa taacttctac    420
ccccgggagg ccaaggtgca gtggaaggtg gataacgctt acagtccgg caacagccaa    480 gaaagcgtga ccgaacaaga tagcaaggac tccacctact ctttatcctc cactttaact    540
ttaagcaagg ccgactacga gaagcataag gtgtacgctt gtgaggtgac ccatcaaggt    600
ttaagcagcc ccgtgaccaa gtccttcaac cggggcgaat gc                       642
```

<210> SEQ ID NO 24
<211> LENGTH: 244
<212> TYPE: PRT
<213> ORGANISM: Artificial Sequence
<220> FEATURE:
<223> OTHER INFORMATION: scFv2

<400> SEQUENCE: 24

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Thr Ile Ser Gly Gly Gly Arg Tyr Thr Tyr Tyr Pro Asp Thr Val
    50                  55                  60

Lys Gly Arg Phe Thr Ile Ser Arg Asp Asn Ala Lys Asn Ser His Tyr
65                  70                  75                  80

Leu Gln Met Asn Ser Leu Arg Ala Glu Asp Thr Ala Val Tyr Phe Cys
                85                  90                  95
```

```
Ala Ser Pro Tyr Gly Gly Tyr Phe Asp Val Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Gly Gly Gly Gly Ser Glu Ile Val Leu Thr Gln Ser
            130                 135                 140

Pro Ala Thr Leu Ser Leu Ser Pro Gly Glu Arg Ala Thr Leu Ser Cys
145                 150                 155                 160

Arg Ala Ser Gln Ser Ile Ser Asn Phe Leu His Trp Tyr Gln Gln Lys
                165                 170                 175

Pro Gly Gln Ala Pro Arg Leu Leu Ile Lys Tyr Ala Ser Gln Ser Ile
            180                 185                 190

Ser Gly Ile Pro Ala Arg Phe Ser Gly Ser Gly Ser Gly Thr Asp Phe
            195                 200                 205

Thr Leu Thr Ile Ser Ser Leu Glu Pro Glu Asp Phe Ala Val Tyr Phe
            210                 215                 220

Cys Gln Gln Ser Asn Ser Trp Pro His Thr Phe Gly Gly Gly Thr Lys
225                 230                 235                 240

Val Glu Ile Lys

<210> SEQ ID NO 25
<211> LENGTH: 709
<212> TYPE: PRT
<213> ORGANISM: Artificial Sequence
<220> FEATURE:
<223> OTHER INFORMATION: heavy chain

<400> SEQUENCE: 25

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
            35                  40                  45

Ala Thr Ile Ser Gly Gly Gly Arg Tyr Thr Tyr Tyr Pro Asp Thr Val
        50                  55                  60

Lys Gly Arg Phe Thr Ile Ser Arg Asp Asn Ala Lys Asn Ser His Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Gly Tyr Phe Asp Val Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Gly Gly Gly Gly Ser Glu Ile Val Leu Thr Gln Ser
            130                 135                 140

Pro Ala Thr Leu Ser Leu Ser Pro Gly Glu Arg Ala Thr Leu Ser Cys
145                 150                 155                 160

Arg Ala Ser Gln Ser Ile Ser Asn Phe Leu His Trp Tyr Gln Gln Lys
                165                 170                 175

Pro Gly Gln Ala Pro Arg Leu Leu Ile Lys Tyr Ala Ser Gln Ser Ile
            180                 185                 190

Ser Gly Ile Pro Ala Arg Phe Ser Gly Ser Gly Ser Gly Thr Asp Phe
            195                 200                 205

Thr Leu Thr Ile Ser Ser Leu Glu Pro Glu Asp Phe Ala Val Tyr Phe
```

-continued

```
              210                 215                 220
Cys Gln Gln Ser Asn Ser Trp Pro His Thr Phe Gly Gln Gly Thr Lys
225                 230                 235                 240
Val Glu Ile Lys Gly Gly Gly Ser Gly Gly Gly Ser Gly Gly
                245                 250                 255
Gly Gly Ser Glu Val Gln Leu Val Glu Ser Gly Gly Leu Val Gln
                260                 265                 270
Pro Gly Gly Ser Leu Arg Leu Ser Cys Ala Ala Ser Gly Phe Asn Ile
                275                 280                 285
Lys Asp Thr Tyr Ile His Trp Val Arg Gln Ala Pro Gly Lys Gly Leu
                290                 295                 300
Glu Trp Val Ala Arg Ile Tyr Pro Thr Asn Gly Tyr Thr Arg Tyr Ala
305                 310                 315                 320
Asp Ser Val Lys Gly Arg Phe Thr Ile Ser Ala Asp Thr Ser Lys Asn
                325                 330                 335
Thr Ala Tyr Leu Gln Met Asn Ser Leu Arg Ala Glu Asp Thr Ala Val
                340                 345                 350
Tyr Tyr Cys Ser Arg Trp Gly Gly Asp Gly Phe Tyr Ala Met Asp Tyr
                355                 360                 365
Trp Gly Gln Gly Thr Leu Val Thr Val Ser Ser Ala Ser Thr Lys Gly
370                 375                 380
Pro Ser Val Phe Pro Leu Ala Pro Ser Ser Lys Ser Thr Ser Gly Gly
385                 390                 395                 400
Thr Ala Ala Leu Gly Cys Leu Val Lys Asp Tyr Phe Pro Glu Pro Val
                405                 410                 415
Thr Val Ser Trp Asn Ser Gly Ala Leu Thr Ser Gly Val His Thr Phe
                420                 425                 430
Pro Ala Val Leu Gln Ser Ser Gly Leu Tyr Ser Leu Ser Ser Val Val
                435                 440                 445
Thr Val Pro Ser Ser Ser Leu Gly Thr Gln Thr Tyr Ile Cys Asn Val
                450                 455                 460
Asn His Lys Pro Ser Asn Thr Lys Val Asp Lys Lys Val Glu Pro Lys
465                 470                 475                 480
Ser Cys Asp Lys Thr His Thr Cys Pro Pro Cys Pro Ala Pro Glu Leu
                485                 490                 495
Leu Gly Gly Pro Ser Val Phe Leu Phe Pro Pro Lys Pro Lys Asp Thr
                500                 505                 510
Leu Met Ile Ser Arg Thr Pro Glu Val Thr Cys Val Val Val Asp Val
                515                 520                 525
Ser His Glu Asp Pro Glu Val Lys Phe Asn Trp Tyr Val Asp Gly Val
                530                 535                 540
Glu Val His Asn Ala Lys Thr Lys Pro Arg Glu Gln Tyr Asn Ser
545                 550                 555                 560
Thr Tyr Arg Val Val Ser Val Leu Thr Val Leu His Gln Asp Trp Leu
                565                 570                 575
Asn Gly Lys Glu Tyr Lys Cys Lys Val Ser Asn Lys Ala Leu Pro Ala
                580                 585                 590
Pro Ile Glu Lys Thr Ile Ser Lys Ala Lys Gly Gln Pro Arg Glu Pro
                595                 600                 605
Gln Val Tyr Thr Leu Pro Pro Ser Arg Glu Glu Met Thr Lys Asn Gln
                610                 615                 620
Val Ser Leu Thr Cys Leu Val Lys Gly Phe Tyr Pro Ser Asp Ile Ala
625                 630                 635                 640
```

Val Glu Trp Glu Ser Asn Gly Gln Pro Glu Asn Asn Tyr Lys Thr Thr
              645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
        675                 680                 685

Val Met His Glu Ala Leu His Asn His Tyr Thr Gln Lys Ser Leu Ser
    690                 695                 700

Leu Ser Pro Gly Lys
705

<210> SEQ ID NO 26
<211> LENGTH: 2127
<212> TYPE: DNA
<213> ORGANISM: Artificial Sequence
<220> FEATURE:
<223> OTHER INFORMATION: heavy chain

<400> SEQUENCE: 26

| | | | | | |
|---|---|---|---|---|---|
| gaggtgaagc | tggtggagtc | cggcggcggc | ctggtgcagc | ctggcggctc | cctgaggctg | 60 |
| tcctgcgccg | cctccggctt | cgccttctcc | tcctacgaca | tgtcctgggt | gaggcaggcc | 120 |
| cctggcaaga | ggctggagtg | ggtggccacc | atctccggcg | gcggcaggta | cacctactac | 180 |
| cctgacaccg | tgaagggcag | gttcaccatc | tccaggggaca | cgccaagaa | ctcccactac | 240 |
| ctgcagatga | actccctgag | ggccgaggac | accgccgtgt | acttctgcgc | ctccccttac | 300 |
| ggcggctact | cgacgtgtg | gggccagggc | accctggtga | ccgtgtcctc | cggcggcggc | 360 |
| ggctccggcg | gcggcggctc | cggcggcggc | ggctccggcg | gcggcggctc | cgagatcgtg | 420 |
| ctgacccagt | cccctgccac | cctgtccctg | tccctggcg | agagggccac | cctgtcctgc | 480 |
| agggcctccc | agtccatctc | caacttcctg | cactggtacc | agcagaagcc | tggccaggcc | 540 |
| cctaggctgc | tgatcaagta | cgcctcccag | tccatctccg | gcatccctgc | caggttctcc | 600 |
| ggctccggct | ccggcaccga | cttcaccctg | accatctcct | cctggagcc | tgaggacttc | 660 |
| gccgtgtact | tctgccagca | gtccaactcc | tggcctcaca | ccttcggcca | gggcaccaag | 720 |
| gtggagatca | agggcggcgg | cggctccggc | ggcggcggct | ccggcggcgg | cggctccgag | 780 |
| gtccaactgg | tggagtccgg | aggaggactg | gtgcaaccg | gcggatccct | ccggctgtct | 840 |
| tgtgctgcta | gcggctttaa | catcaaggat | acctatatcc | attgggttag | gcaagctccc | 900 |
| ggtaagggct | agaatgggt | cgctaggatc | taccccacca | atggctatac | tcgttacgcc | 960 |
| gacagcgtga | agggtcggtt | caccatctcc | gctgacacct | ccaagaacac | agcttacctc | 1020 |
| caaatgaact | ctttacgggc | cgaggacaca | gccgtgtact | actgttcccg | gtggggaggc | 1080 |
| gacggcttct | atgctatgga | ttactggggc | caaggtactt | tagtgacagt | gtccagcgcc | 1140 |
| agcacaaaag | gaccttccgt | cttccctctg | gctccctcct | ccaagagcac | cagcggcgga | 1200 |
| acagctgctc | tcggctgtct | ggtgaaggac | tacttccccg | aacccgttac | cgtgtcttgg | 1260 |
| aattccggcg | ctttaaccct | cggcgtgcac | acctttccg | ctgttttaca | gagcagcggc | 1320 |
| ctctattctt | taagctccgt | ggtcacagtg | ccttcctcct | ccctgggcac | ccagacctac | 1380 |
| atctgcaacg | tgaaccacaa | gccttccaac | accaaggtgg | acaagaaggt | ggagcctaag | 1440 |
| tcctgcgaca | agacccacac | ctgccctcct | tgccctgccc | ctgagctgct | gggcggccct | 1500 |
| tccgtgttcc | tgttccctcc | taagcctaag | gacaccctga | tgatctccag | gacccctgag | 1560 |
| gtgacctgcg | tggtggtgga | cgtgtcccac | gaggaccctg | aggtgaagtt | caactggtac | 1620 |

```
gtggacggcg tggaggtgca caacgccaag accaagccta gggaggagca gtacaactcc    1680
acctacaggg tggtgtccgt gctgaccgtg ctgcaccagg actggctgaa cggcaaggag    1740
tacaagtgca aggtgtccaa caaggccctg cctgcccta tcgagaagac catctccaag     1800
gccaagggcc agcctaggga gcctcaggtg tacaccctgc ctccttccag ggaggagatg    1860
accaagaacc aggtgtccct gacctgcctg gtgaagggct tctacccttc cgacatcgcc    1920
gtggagtggg agtccaacgg ccagcctgag aacaactaca agaccacccc tcctgtgctg    1980
gactccgacg gctccttctt cctgtactcc aagctgaccg tggacaagtc caggtggcag    2040
cagggcaacg tgttctcctg ctccgtgatg cacgaggccc tgcacaacca ctacacccag    2100
aagtccctgt ccctgtcccc tggcaag                                        2127
```

ANTI-HER2/PD1 BISPECIFIC ANTIBODY

RELATED APPLICATIONS

This application is a national phase application claiming benefit of priority under 35 U.S.C. § 371 to International (PCT) Patent Application serial number PCT/CN2019/112467, filed Oct. 22, 2019, which claims benefit of priority to Chinese Patent Application No. CN 201811376950.9, filed Nov. 19, 2018. The aforementioned applications are expressly incorporated herein by reference in their entirety and for all purposes.

FIELD OF THE INVENTION

The invention belongs to the field of tumor treatment and biotechnology, and relates to an anti-HER2 and PD1 bispecific antibody molecule, preparation method and application thereof.

BACKGROUND OF THE INVENTION

HER2 (human epidermal growth factor receptor 2) has tyrosine protein kinase activity, which is a member of the human epidermal growth factor receptor family. It is expressed at low levels in only a few normal tissues in adults. However, studies have shown that HER2 is overexpressed in a variety of tumors, for example, such overexpression is present in about 30% of breast cancer patients and 16% of gastric cancer patients. The overexpression of HER2 in tumors can significantly promote tumor angiogenesis, tumor growth, and enhance tumor invasion and metastasis, which is an important indicator of poor prognosis for such patients. Thus, as early as 1998, Herceptin (Genentech/Roche), the first HER2-targeting monoclonal antibody drug, was approved by the FDA for the treatment of HER2-overexpressing breast cancer and gastric cancer.

Human programmed cell death protein 1 (PD-1) is a type I membrane protein consisting of 288 amino acids, the extracellular segment is the Ig variable (V-type) domain responsible for binding ligands, and the intracellular segment is the cytoplasmic tail region responsible for binding signal transduction molecules. The cytoplasmic tail region of PD1 contains two tyrosine-based signal transduction motifs, namely ITIM (Immune Receptor Tyrosine Inhibition Motif) and ITSM (Immune Receptor Tyrosine Transduction Motif). PD-1 is expressed on the surface of activated T lymphocytes, binds to the ligands PD-L1 (programmed cell death-Ligand 1) and PD-L2 (programmed death receptor-Ligand 2) to inhibit the activity of T lymphocytes and related cellular immune responses in vivo. Numerous studies have shown that the interaction of PD-1 and PD-L1 not only maintains the balance of the immune system in the body, but is also the main mechanism that causes tumor cells that express PD-L1 to evade immune surveillance. By blocking the PD1/PD-L1 signaling pathway, the immune system can be activated and the immune killing function of T cells can be restored.

KEYTRUDA® (pembrolizumab) is the first humanized monoclonal antibody against PD-1 on the market, which was approved by the FDA in September 2014 for the treatment of melanoma, and the indications approved until 2018 include: melanoma, non-small cell lung cancer, Hodgkin's lymphoma, head and neck squamous cell carcinoma, bladder cancer, gastric cancer, and solid tumors with MSI-H or dMMR. OPDIVO® (nivolumab) is a anti-PD1 monoclonal antibody of Bristol-Myers Squibb, which was approved for marketing by the FDA in December 2014, and the indications include: melanoma, non-small cell lung cancer, renal cell carcinoma, classic Hodgkin's lymphoma tumor, head and neck squamous cell carcinoma, bladder cancer, colorectal cancer and hepatocellular carcinoma. The anti-PD1 monoclonal antibody independently developed by Sunshine Guojian is a new humanized anti-PD1 monoclonal antibody. In vivo and in vitro biological activity and anti-tumor activity studies have shown that the biological activity of anti-PD1 is between the positive control drugs Opdivo and Keytruda, and is slightly better than the positive control drug Opdivo in some aspects.

Bispecific antibody (BsAb) refers to an antibody molecule that can bind two (or more) different epitopes at the same time. Compared with traditional monoclonal antibodies, bispecific antibodies have unique mechanisms of action: 1) Bispecific antibodies can bind to two or more different antigen molecules or different epitopes of the same molecule at the same time, but combination therapy often do not have this effect. 2) Bispecific antibodies mediate the interaction between cells, they can bind to two antigens on effector cells and target cells, respectively, build a bridge between effector cells and target cells, and promote the interaction between the cells, for example, mediate killing of tumor cells by immune cells. Therefore, bispecific antibodies have unique advantages that traditional monoclonal antibodies do not possess.

SUMMARY OF THE INVENTION

The present invention provides a new bispecific antibody that can specifically bind to HER2 and PD1, and also provides the preparation method and application of the bispecific antibody.

Therefore, the object of the present invention is to provide a bispecific antibody that can specifically bind to HER2 and PD1; provide a nucleotide molecule encoding the bispecific antibody; provide an expression vector comprising the nucleotide molecule; provide a host cell comprising the expression vector; provides a method of preparing the bispecific antibody; provides a pharmaceutical composition comprising the bispecific antibody; provides an application of the bispecific antibody in the preparation of a medicine.

In order to achieve the above objects, the present invention adopts the following technical solutions:

One aspect of the present invention provides a bispecific antibody capable of specifically binding to HER2 and PD1, which comprises an immunoglobulin antibody IgG and two identical single-chain variable region fragments scFv, wherein each single-chain variable fragment scFv comprises a variable region VH and a variable region VL, VH and VL are connected by a peptide linker L1, and each single-chain variable fragment scFv is connected in series with the immunoglobulin antibody IgG by a linker peptide L2.

The "bispecific antibody" in the present invention refers to a bispecific antibody that has two different antigen-binding sites and can simultaneously bind to HER2 and PD1, which comprises two single-chain variable fragments scFv and an immunoglobulin antibody IgG conjugated to it. Each scFv is connected to each heavy chain of immunoglobulin antibody IgG by a peptide linker L2 to form a heavy chain fusion protein of the bispecific antibody, wherein each scFv contains a variable region VH and a variable region VL, and VH and VL are connected by a peptide linker L1.

The "single-chain variable region fragment scFv" in the present invention refers to a fusion protein comprising the variable regions of the immunoglobulin heavy chain VH and light chain VL. VH and VL are connected by a peptide linker, wherein the fusion protein retains the same antigen specificity as the intact immunoglobulin.

The "immunoglobulin antibody IgG" in the present invention is a molecule of about 150 kDa, which is composed of four peptide chains, containing two identical heavy chains of about 50 kDa and two identical light chains of about 25 kDa, thus having a tetrameric quaternary structure. The two heavy chains are connected to each other by disulfide bonds, and each of them is connected to a light chain. The resulting tetramer has the same two halves, which form a fork or Y-like shape, and each end of the fork contains the same antigen-binding site. IgG antibodies can be divided into multiple subclasses (for example, IgG1, 2, 3, 4) based on small differences in the amino acid sequence of the constant region of the heavy chain.

As a preferred embodiment, VH comprises complementarity determining regions HCDR1-3, wherein HCDR1 has the the amino acid sequence as shown in SEQ ID NO: 1, HCDR2 has the amino acid sequence as shown in SEQ ID NO: 2, and HCDR3 has the amino acid sequence as shown in SEQ ID NO: 3;

the VL comprises complementarity determining regions LCDR1-3, wherein LCDR1 has the amino acid sequence as shown in SEQ ID NO: 4, LCDR2 has the amino acid sequence as shown in SEQ ID NO: 5, and LCDR3 has the amino acid sequence as shown in SEQ ID NO: 6;

the heavy chain of the immunoglobulin antibody IgG comprises complementarity determining regions HCDR4-6, wherein HCDR4 has the amino acid sequence as shown in SEQ ID NO: 7, wherein HCDR5 has the amino acid sequence as shown in SEQ ID NO: 8, wherein HCDR6 has the amino acid sequence as shown in SEQ ID NO: 9;

the light chain of the immunoglobulin antibody IgG comprises complementarity determining regions LCDR4-6, wherein LCDR4 has the amino acid sequence as shown in SEQ ID NO: 10, wherein LCDR5 has the amino acid sequence as shown in SEQ ID NO: 11, wherein LCDR6 has the amino acid sequence as shown in SEQ ID NO: 12;

In the art, the binding region of an antibody usually comprises one light chain variable region and one heavy chain variable region, and each variable region comprises 3 CDR domains. The CDR domains of heavy chain and light chain of an antibody are called HCDR and LCDR, respectively. Therefore, a conventional antibody antigen binding site comprises six CDRs, including a set of CDRs from the heavy and light chain V regions, respectively.

As a preferred embodiment, the scFv has the amino acid sequence of VH as shown in SEQ ID NO: 13, the amino acid sequence of VL as shown in SEQ ID NO: 14; the immunoglobulin antibody IgG has the amino acid sequence of the heavy chain variable region as shown in SEQ ID NO: 15, and the amino acid sequence of the light chain variable region is shown in SEQ ID NO: 16.

As a preferred embodiment, the peptide linker L1 has the amino acid sequence as shown in SEQ ID NO: 17.

As a preferred embodiment, the peptide linker L2 has the amino acid sequence as shown in SEQ ID NO: 18.

As a preferred embodiment, the single-chain variable fragment scFv1 has the molecular structure of VL-L1-VH, and the N-terminus of each scFv is connected to the C-terminus of the heavy chain of immunoglobulin antibody IgG by a peptide linker L2.

As a preferred embodiment, the single-chain variable fragment scFv1 has the amino acid sequence as shown in SEQ ID NO: 19.

As a preferred embodiment, the bispecific antibody has the amino acid sequence of the heavy chain as shown in SEQ ID NO: 20, and the amino acid sequence of the light chain as shown in SEQ ID NO: 21.

As a preferred embodiment, the single-chain variable fragment scFv2 has the molecular structure of VH-L1-VL, and the C-terminus of each scFv is connected to the N-terminus of the heavy chain of immunoglobulin antibody IgG by a peptide linker L2.

As a preferred embodiment, the single-chain variable fragment scFv2 has the amino acid sequence as shown in SEQ ID NO: 24.

As a preferred embodiment, the bispecific antibody has the amino acid sequence of the heavy chain as shown in SEQ ID NO: 25, and the amino acid sequence of the light chain as shown in SEQ ID NO: 21.

When constructing the bispecific antibody of the present invention, the problems related to the chemical and physical stability of the bispecific antibody are also solved, such as expressing physically stable molecules, increasing heat and salt-dependent stability, reducing aggregation, increasing solubility at high concentrations, and maintaining affinity for the two antigens HER2 and PD1, etc.

Another aspect of the present invention provides a nucleotide molecule, which encodes the above-mentioned bispecific antibody.

As a preferred embodiment, the nucleotide molecule has the nucleotide sequence encoding the heavy chain of the bispecific antibody capable of specifically binding to HER2 and PD1 as shown in SEQ ID NO: 22, and the nucleotide sequence encoding the light chain thereof as shown in SEQ ID NO: 23; or the nucleotide molecule has the nucleotide sequence encoding the heavy chain of the bispecific antibody capable of specifically binding to HER2 and PD1 as shown in SEQ ID NO: 26, and the nucleotide sequence encoding the light chain thereof as shown in SEQ ID NO: 23.

The preparation method of the nucleotide molecule of the present invention is a conventional preparation method in the art, and preferably includes the following preparation methods: the nucleotide molecule encoding the above-mentioned monoclonal antibody is obtained by gene cloning technology such as PCR method, or the nucleotide molecule encoding the above-mentioned monoclonal antibody is obtained by artificial full-sequence synthesis.

Those skilled in the art know that the nucleotide sequence encoding the amino acid sequence of the bispecific antibody can be replaced, deleted, altered, inserted or added as appropriate to provide a polynucleotide homologue. The polynucleotide homologue of the present invention can be prepared by replacing, deleting or adding one or more bases of the genes encoding the bispecific antibody within the scope of maintaining the activity of the antibody.

Another aspect of the present invention provides an expression vector, which comprises the above-mentioned nucleotide molecule.

The expression vector is a conventional expression vector in the art, which refers to an expression vector containing appropriate regulatory sequences, such as promoter sequences, terminator sequences, polyadenylation sequences, enhancer sequences, marker genes and/or sequences, and other appropriate sequences. The expression vector can be a virus or a plasmid, such as an appropriate phage or phagemid. For more technical details, please refer to, for example, Sambrook et al., Molecular Cloning: A Laboratory Manual, Second Edition, Cold Spring Harbor Laboratory Press, 1989. For many known techniques and protocols for nucleic acid manipulation, please refer to Current Protocols in Molecular Biology, Second Edition, edited by Ausubel et al. The expression vector of the present invention is preferably pDR1, pcDNA3.1(+), pcDNA3.1/ZEO (+), pDHFR, pTT5, pDHFF, pGM-CSF or pCHO 1.0, more preferably pTT5.

In addition, the present invention provides a host cell, which comprises the above expression vector.

The host cell of the present invention may be a variety of conventional host cells in the field, as long as it can make the above-mentioned recombinant expression vector stably replicate itself and the nucleotides carried by it can be effectively expressed. Wherein the host cell includes prokaryotic expression cells and eukaryotic expression cells, and the expression vector preferably includes: COS, CHO (Chinese Hamster Ovary), NS0, sf9, sf21, DH5α, BL21 (DE3) or TG1, more preferably $E. coli$ TG1, BL21(DE3) cells (expressing single-chain antibodyies or Fab antibodies) or CHO-K1 cells (expressing full-length IgG antibodies). The above expression vector may be transformed into a host cell to obtain the preferred recombinant expression transformant of the present invention. The transformation method may be a conventional transformation method in the art, preferably a chemical transformation method, a heat shock method or an electrotransformation method.

As a preferred embodiment, the host cell is a eukaryotic cell. Preferred are CHO cells or 293E cells.

Another aspect of the present invention provides a method of preparing the above bispecific antibody capable of specifically binding to HER2 and PD1, and the preparation method comprises the following steps of:
a) under expression conditions, cultivating the above host cell, to express the bispecific antibody capable of specifically binding to HER2 and PD1;
b) isolating and purifying the bispecific antibody of step a).

The method of culturing the host cell and the method of isolating and purifying the antibody of the present invention may be a conventional method in the art. For the specific operation method, please refer to the corresponding cell culture technical manual and antibody isolation and purification technical manual. The preparation method of the anti-HER2/PD1 bispecific antibody disclosed in the present invention comprises: culturing the above-mentioned host cell under expression conditions so as to express the bispecific antibody capable of specifically binding to HER2 and PD1; and isolating and purifying the anti-HER2/PD1 bispecific antibody. Using the above method, the recombinant protein can be purified into a substantially homogeneous substance, for example, showing a single band on SDS-PAGE electrophoresis.

The anti-HER2/PD1 bispecific antibody disclosed in the present invention can be isolated and purified by affinity chromatography. According to the characteristics of the affinity column used, conventional methods such as high-salt buffer, pH change, etc. may be used to elute the anti-HER2/PD1 bispecific antibody bound on the affinity column. The inventors of the present invention conducted detection experiments on the obtained anti-HER2/PD1 bispecific antibody, and the experimental results show that the anti-HER2/PD1 bispecific antibody can bind to target cells and antigens well and has a high affinity.

Another aspect of the present invention provides a composition, which comprises the above bispecific antibody capable of specifically binding to HER2 and PD1 and one or more pharmaceutically acceptable carriers, diluents or excipients.

The bispecific antibody of the present invention can be combined with a pharmaceutically acceptable carrier to form a pharmaceutical preparation composition, so as to exert a therapeutic effect more stably. These preparations can ensure the conformational integrity of the amino acid core sequences of the bispecific antibody of the present invention, and meanwhile, protect the multifunctional groups of the protein from degradation (including but not limited to aggregation, deamination or oxidation). Generally, for liquid formulations, it can be stored at 2° C.-8° C. for at least one year, and for freeze-dried formulations, it can be stored at 30° C. for at least six months. The bispecific antibody preparation may be suspension, water injection, freeze-dried and other preparations commonly used in the pharmaceutical field.

For the water injection or freeze-dried preparation of the bispecific antibody of the present invention, pharmaceutically acceptable carriers preferably include, but are not limited to: one of surfactants, solution stabilizers, isotonic regulators, and buffers or a combination thereof. The surfactants preferably include but are not limited to: nonionic surfactants such as polyoxyethylene sorbitan fatty acid ester (Tween 20 or 80); poloxamer (e.g. poloxamer 188); Triton; sodium dodecyl sulfate (SDS); sodium lauryl sulfate; tetradecyl, linoleyl or octadecylsarcosine; Pluronics; MONAQUAT™, etc., which should be added in an amount such that the granulation tendency of the anti-HER2/PD1 bispecific antibody is minimized. The solution stabilizers preferably include but are not limited to one or a combination of the following: sugars, for example, reducing sugars and non-reducing sugars; amino acids, for example, monosodium glutamate or histidine; alcohols, for example, triols, higher sugar alcohols, propylene glycol, polyethylene glycol, etc. The solution stabilizer should be added in an amount such that the final formed preparation remains stable for a period of time that is considered stable by those skilled in the art. Isotonicity adjusting agents preferably include but are not limited to, one of sodium chloride, and mannitol, or a combination thereof. The buffers preferably include but are not limited to, one of Tris, histidine buffer, and phosphate buffer, or a combination thereof.

Another aspect of the present invention provides the use of the above bispecific antibody capable of specifically binding to HER2 and PD1, or the above pharmaceutical composition in the preparation of a medicine, the medicine is used for the treatment of cancers or tumors.

The medicine used for the treatment of cancers or tumors of the present invention refers to a medicine that inhibits and/or treats tumors, which may include delay in the development of tumor-related symptoms and/or reduction in the severity of these symptoms, and further include reduction of symptoms associated with pre-existing tumors and prevention of other symptoms, and also include reduction or prevention of tumor metastasis.

The tumors targeted by the medicine of the present invention preferably include, but are not limited to: lung cancer, bone cancer, stomach cancer, pancreatic cancer, skin cancer, head and neck cancer, uterine cancer, ovarian cancer, testicular cancer, uterine cancer, fallopian tube cancer, uterus endometrial cancer, cervical cancer, vaginal cancer, vulvar cancer, rectal cancer, colon cancer, anal cancer, breast cancer, esophageal cancer, small intestine cancer, endocrine system cancer, thyroid cancer, parathyroid cancer, adrenal cancer, urethral cancer, penile cancer, prostate cancer, pancreatic cancer, brain cancer, testicular cancer, lymphoma, transitional cell cancer, bladder cancer, kidney cancer or ureteral cancer, renal cell cancer, renal pelvis cancer, Hodgkin's disease, non-Hodgkin's lymphoma, soft tissue sarcoma, solid tumors in children, lymphocytic lymphoma, central nervous system (CNS) tumor, primary central nervous system lymphoma, tumor angiogenesis, spinal tumor, brainstem glioma, pituitary adenoma, melanoma, Kaposi's sarcoma, epidermoid carcinoma, squamous cell carcinoma, T-cell lymphoma, chronic or acute leukemia, and combinations of said cancers.

When the bispecific antibody and its composition of the present invention are administered to animals including humans, the dose may vary depending on the age and weight of the subject, the characteristics and severity of the disease, and the route of administration. The results of animal experiments and various situations may be referred, the total dose cannot exceed a certain range. Specifically, the dose of intravenous injection is 1-1800 mg/day.

The bispecific antibody and its composition of the present invention can also be administered in combination with other anti-tumor drugs to achieve the purpose of more effective treatment of tumors. Such anti-tumor drugs include but are not limited to: 1. cytotoxic drugs: 1) drugs that act on the chemical structure of nucleic acids: alkylating agents such as nitrogen mustards, nitrosoureas, and methylsulfonates; platinum compounds such as Cisplatin, Carboplatin and Oxaliplatin, etc.; antibiotics such as Adriamycin/Doxorubicin, Dactinomycin D, Daunorubicin, Epirubicin, Mithramycin, etc.; 2) drugs that affect nucleic acid metabolism: dihydrofolate reductase inhibitors such as Methotrexate (MTX) and Pemetrexed, etc.; thymidine synthase inhibitors such as fluorouracils (5-fluorouracil, Capecitabine), etc.; purine nucleoside synthase inhibitors such as 6-mercaptopurine, etc.; nucleotide reductase inhibitors such as Hydroxycarbamide, etc.; DNA polymerase inhibitors such as Cytosinearabinoside and Gemcitabine, etc.; 3) drugs that act on tubulin: Docetaxel, Vincristine, Vinorelbine, podophyllin, homoharringtonine, etc.; 2. hormonal drugs: anti-estrogens such as Tamoxifen, Droloxifene, Exemestane, etc.; aromatase inhibitors such as Aminoglutethimide, Formestane, Letrozle, Anastrozole, etc.; anti-androgens: flutamine RH-LH agonist/antagonist: Norride, Enanton, etc.; 3. biological response modifier drugs: these drugs mainly regulate the immune function of the body to achieve anti-tumor effects, such as Interferon; Interleukin-2; Thymosins, etc.; 4. monoclonal antibody drugs: Trastuzumab, Rituximab, Cetuximab, Bevacizumab, etc.; 5. other anti-tumor drugs: including some drugs whose mechanisms are not yet clear and need to be further studied. The bispecific antibody and its composition disclosed in the present invention can be used in combination with one or a combination of the above anti-tumor drugs.

The present invention provides a bispecific antibody that combines traditional tumor targeted therapies with immune checkpoint blockades (PD1/PDL1). Anti-HER2/PD1 bispecific antibody simultaneously bound to and bridged the two targets in vitro as well as on the cell surface without loss of affinities in comparison with its respective parental mAb. Further, the BsAb retained the biological activities of each of its parental mAb: it was as effective as the parental mAb in inhibiting proliferation of HER2-expressing tumor cells and in activating T cells via blockading PD1/PDL1 interaction. In animal studies, the BsAb demonstrated equal potency to trastuzumab in a nude mouse xenografted tumor model (a system without human T cell presence), and to the anti-PD1 mAb (609 A) in the human PD1-transgenic mouse syngeneic tumor model (where the tumor cells does not express human HER2).

The positive and progressive effect of the present invention is that the HER2/PD1 bispecific antibody can simultaneously exert three effects and play a synergistic role in killing tumors. First, it blockade the PD-1/PD-L1 signaling pathway. PD-L1 is expressed on tumor cells and some immune regulatory cells, while PD-1 is expressed on T cells. The binding of PD-1 and PD-L1 can inhibit the proliferation and activation of T cells. Blockading this pathway can restore the immune killing function of T cells. Second, the Fc segment of anti-HER2 antibody of this bispecific antibody can bind to the Fc receptors of NK and other cells, allowing the immune effector cells of the Fc receptor to show ADCC effects, killing of tumor cells, but no obvious killing of T cells. Third, the anti-HER2 activity of the bispecifc antibody can bind to tumor cells that over-express HER2 antigen and inhibit tumor proliferation. In summary, the HER2/PD1 bispecific antibody can simultaneously bind to PD1 and HER2 antigens, blockade signal pathways, and activate immune effector cells, which work together to inhibit and kill tumor cells. Anti-HER2/PD1 bispecific antibody—also has good stability.

DETAILED DESCRIPTION OF THE INVENTION

Figure 1A:
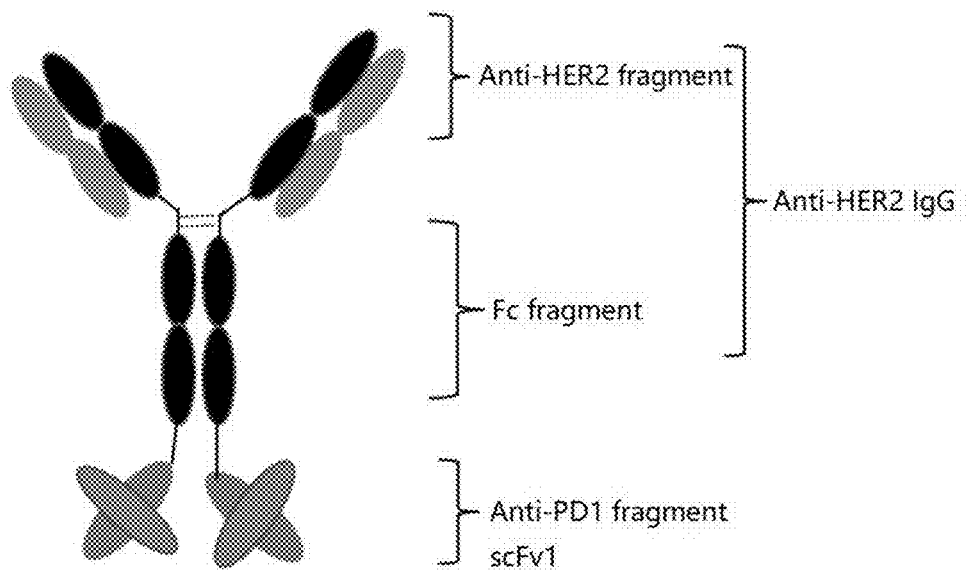
FIG. 1A: Schematic diagram of the structure of anti-HER2/PD1 bispecific antibody-a

The following examples and experimental examples are intended to further illustrate the present invention, and should not be construed as limiting the present invention. The examples do not include detailed descriptions of traditional methods, such as those methods of constructing vectors and plasmids, methods of inserting genes encoding proteins into such vectors and plasmids or methods of introducing plasmids into host cells. Such methods are well known to those of ordinary skill in the art, and are described in many publications, including Sambrook, J., Fritsch, E. F. and Maniais, T. (1989) Molecular Cloning: A Laboratory Manual, 2nd edition, Cold spring Harbor Laboratory Press.

The experimental materials and sources and the preparation methods of the experimental reagents used in the following examples are specifically described as follows.

Experimental Materials:
  CHO cells: purchased from Thermo fisher company, catalog number A29133.
  293E cells: from NRC biotechnology Research Institute.
  Human breast cancer cell BT474: from the Cell Bank of Chinese Academy of Sciences, catalog number TCHu143.
  PD-L1aAPC/CHO-K1 cells: purchased from Promega, catalog number J1252.
  CD4+ T cells: purchased from Allcells, catalog number LP180329.
  NK92 cells: purchased from ATCC, product number pta8837.
  Protein A chip: label No: 29139131-AA; lot: 10261132.
  SD rats: purchased from Zhejiang Weitong Lihua Laboratory Animal Technology Co., Ltd., production license SCXK (Zhejiang) 2018-0001.
  Human gastric cancer cell line NCI-N87: purchased from the American Type Culture Collection (ATCC).
  BALB/c nude mice: purchased from Shanghai Lingchang Biological Technology Co., Ltd.
  MC38 mouse colon cancer cell line: Heyuan Biotechnology (Shanghai) Co., Ltd.
  Humanized PD1 mouse strain C57BJ/6J-PDCD1em1 (Hpdcd1)/Smoc: product number: NM-KI-00015, purchased from Shanghai Southern Model Biotechnology Co., Ltd.
  PBMC: purchased from Sailybio, catalog number SLB-HP040A.

Experimental Reagents:
  HRP-labeled mouse anti-human Fab antibody: purchased from sigma, catalog number A0293.
  Streptavidin HRP: purchased from BD Biosciences, catalog number 554066.
  Goat anti-human IgG-FITC: purchased from sigma, catalog number F4143.
  Anti-CD28 antibody: purchased from Abcam, catalog number ab213043.
  IL-2: purchased from R&D, catalog number 202-IL.
  PBS: purchased from Sangon Biotech (Shanghai) Co., Ltd., catalog number B548117.
  PBST: PBS+0.05% Tween 20.
  BSA: purchased from Sangon Biotech (Shanghai) Co., Ltd., catalog number A60332.
  TMB: purchased from BD company, catalog number 555214.
  Bio-Glo: purchased from Promega, catalog number G7940.
  FBS: purchased from Gibco, catalog number 10099.
  HBS-EP working solution: purchased from Life science, BR-1006-69.
  CellTiter-Glo: purchased from promega, catalog number G775B.

Laboratory Apparatus:
  HiTrap MabSelectSuRe column: purchased from GE company.
  Beckman Coulter CytoFLEX flow cytometer: purchased from Beckman company.
  SpectraMax i3x microplate reader: purchased from Molecular Devices company.
  SpectraMaxM5 microplate reader: purchased from Molecular Devices company.
  Micro-calorimeter scanning calorimeter: MicroCal VP-Capillary DSC The HER2 monoclonal antibody in the examples of the present invention refers to a human-mouse chimeric monoclonal antibody obtained by Sunshine Guojian Pharmaceutical company according to the amino acid sequence of Herceptin, according to the same expression and purification method as that of the double antibody in Example 2. The PD1 monoclonal antibody in the examples of the present invention refers to a brand-new anti-PD1 humanized monoclonal antibody disclosed in Chinese patent application CN201710054783.5, which is independently developed by Sunshine Guojian Pharmaceutical company.

Example 1. Construction of Anti-HER2/PD1 Bispecific Antibody Molecule

In the present invention, the anti-HER2/PD1 bispecific antibody-a was constructed by connecting anti-HER2 monoclonal antibody IgG and the scFv of anti-PD1 monoclonal antibody in series.

The light chain variable region VL (SEQ ID NO: 14) and heavy chain variable region VH (SEQ ID NO: 13) of the anti-PD1 monoclonal antibody were connected by peptide linker L1 (SEQ ID NO: 17), to obtain the anti-PD1 single-chain antibody fragment VL-L1-VH, i.e., the anti-PD1 fragment scFv1 (SEQ ID NO: 19). The single-chain antibody fragment and the heavy chain of the anti-HER2 monoclonal antibody were connected by L2 (SEQ ID NO: 18), to obtain the heavy chain of the bispecific antibody molecule anti-HER2/PD1 bispecific antibody-a (SEQ ID NO: 20), and the light chain of the anti-HER2 monoclonal antibody (SEQ ID NO: 21) remains unchanged. In order to improve the expression efficiency of antibody molecule in CHO cells, Genewiz company was entrusted to perform codon optimization of the nucleic acid sequence of anti-HER2/PD1 bispecific antibody-a molecule. During the optimization, factors such as codon preference, GC content, mRNA secondary structure, repetitive sequence, etc. were mainly considered. Then Genewiz company was entrusted to synthesize the genes. Anti-HER2/PD1 bispecific antibody-a has the nucleic acid sequence of the heavy chain as shown in SEQ ID NO: 22, and the nucleic acid sequence of the light chain as shown in SEQ ID NO: 23. The structure of anti-HER2/PD1 bispecific antibody-a is shown in FIG. 1A, and the sequence is shown in the attached sequence listing.

Figure 1B:
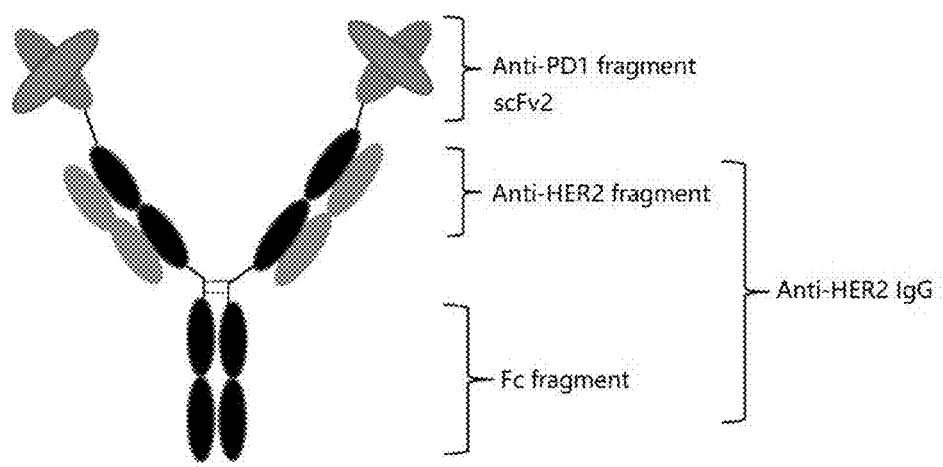
FIG. 1B: Schematic diagram of the structure of anti-HER2/PD1 bispecific antibody-b

The molecular construction of anti-HER2/PD1 bispecific antibody-b is as follows:

The light chain variable region VL (SEQ ID NO: 14) and heavy chain variable region VH (SEQ ID NO: 13) of the anti-PD1 monoclonal antibody were connected by peptide linker L1 (SEQ ID NO: 17), to obtain the anti-PD1 single-chain antibody fragment VH-L1-VL, i.e., the anti-PD1 fragment scFv2 (SEQ ID NO: 24). The single-chain antibody fragment and the heavy chain of the anti-HER2 monoclonal antibody were connected by L2 (SEQ ID NO: 18), to obtain the heavy chain of the bispecific antibody molecule anti-HER2/PD1 bispecific antibody-b (SEQ ID NO: 25), and the light chain of the anti-HER2 monoclonal antibody (SEQ ID NO: 21) remains unchanged. In order to improve the expression efficiency of antibody molecule in CHO cells, Genewiz company was entrusted to perform codon optimization of the nucleic acid sequence of anti-HER2/PD1 bispecific antibody-b molecule. During the optimization, factors such as codon preference, GC content, mRNA secondary structure, repetitive sequence, etc. were mainly considered. Then Genewiz company was entrusted to synthesize the genes. Anti-HER2/PD1 bispecific antibody-b has the nucleic acid sequence of the heavy chain as shown in SEQ ID NO: 26, and the nucleic acid sequence of the light chain as shown in SEQ ID NO: 23. The structure of anti-HER2/PD1 bispecific antibody-b is shown in FIG. 1B, and the sequence is shown in the attached sequence listing.

Example 2. Expression and Purification of Bispecific Antibody

Figure 2A:
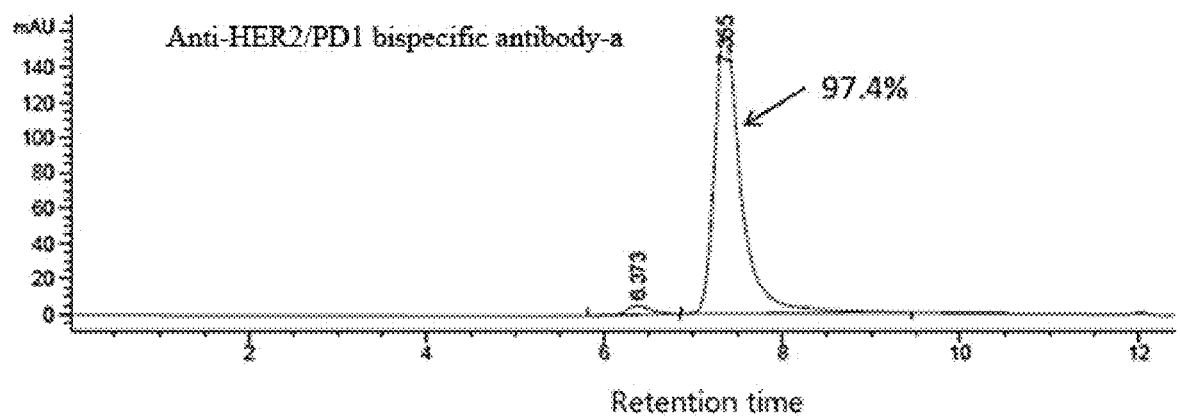
FIG. 2A: HPLC detection pattern of anti-HER2/PD1 bispecific antibody-a
Figure 2B:
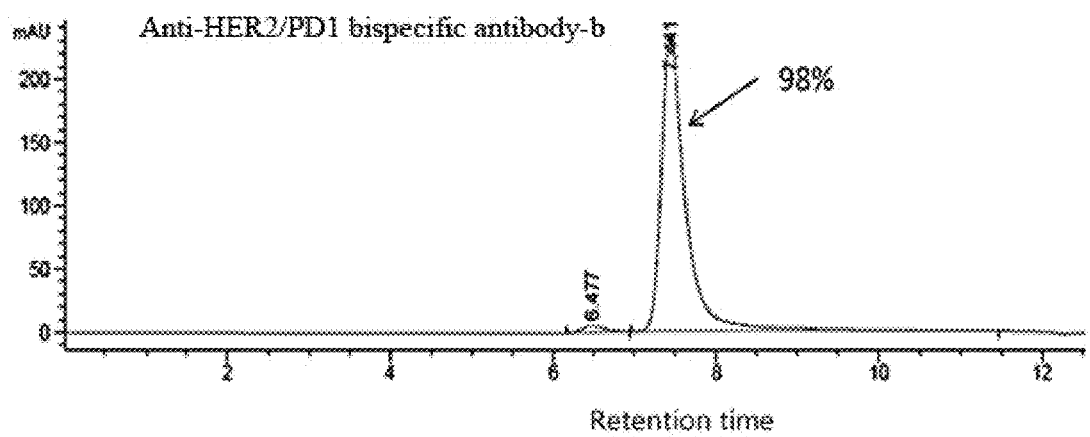
FIG. 2B: HPLC detection pattern of anti-HER2/PD1 bispecific antibody-b
Figure 2C:
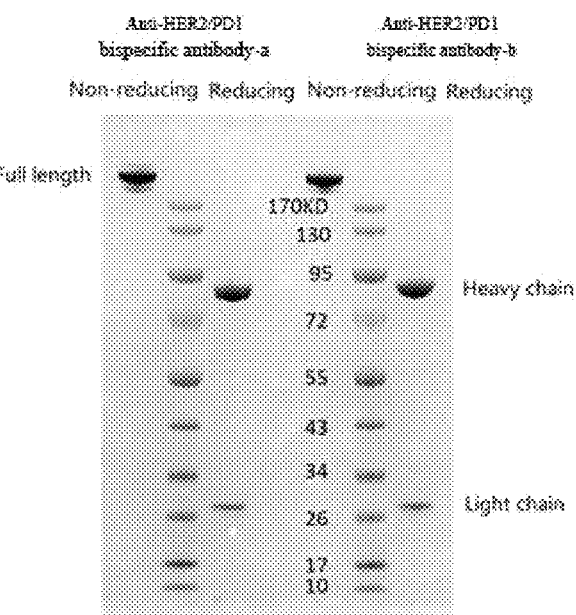
FIG. 2C: SDS-PAGE detection results of anti-HER2/PD1 bispecific antibody-a and b

The DNA fragments of the heavy and light chains of the bispecific antibodies were subcloned into pTT5 vector, and the recombinant plasmids were extracted and co-transfected into CHO cells and/or 293E cells. After the cells were cultured for 5-7 days, the culture solutions were centrifuged at high speed, vacuum filtered with a microporous membrane, and loaded onto HiTrap MabSelectSuRe column. The proteins were eluted in one step with an eluent containing 100 mM citric acid, pH 3.5, and the target samples were recovered and dialyzed against PBS (pH 7.4). The purified proteins were detected by HPLC. The HPLC detection patterns of anti-HER2/PD1 bispecific antibodies-a and b are shown in FIGS. 2A and 2B, respectively. The antibody molecules are in uniform state and the monomer purity is over 97%. The purified anti-HER2/PD1 bispecific antibody-a and b were added with non-reducing electrophoresis buffer and detected by SDS-polyacrylamide gel electrophoresis; the purified anti-HER2/PD1 bispecific antibody-a and -b were added with reducing electrophoresis buffer and boiled, and detected by SDS-polyacrylamide gel electrophoresis. The electropherogram is shown in FIG. 2C. The theoretical molecular weight of the full-length bispecific antibodies is 199 KD.

Example 3. Determination of the Affinity of Bispecific Antibody to Antigen by Enzyme-Linked Immunosorbent Assay (ELISA)

Figure 3A:
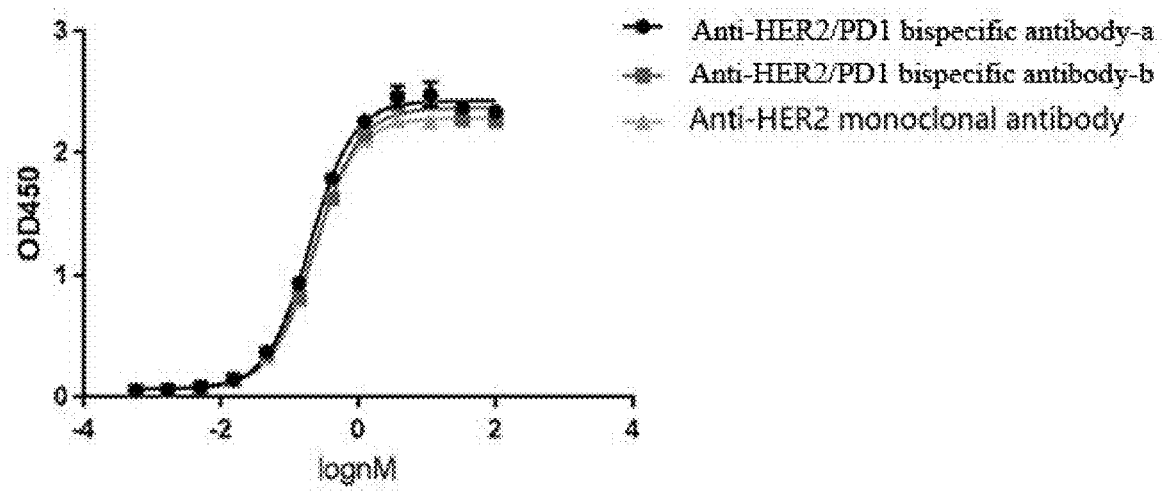
FIG. 3A: Binding of anti-HER2/PD1 bispecific antibody-a, -b to HER2 detected by ELISA

In order to detect the binding affinity of anti-HER2/PD1 bispecific antibody-a and -b to the HER2 antigen, the HER2-ECD-His protein (prepared by Sunshine Guojian) was diluted to 250 ng/ml with PBS buffer (pH7.4), and then added into an ELISA plate at 100 μl/well; incubated overnight at 4° C.; the next day, the plate was washed twice with PBST; each well was blocked by adding PBST+1% BSA at 37° C. for 1 h; the plate was washed twice with PBST; then the antibody to be tested that was gradiently diluted with PBS+1% BSA was added, using HER2 monoclonal antibody as positive control, with an initial concentration of 100 nM, gradually diluted 3-fold for a total of 12 gradients, incubated at 37° C. for 1 h. The plate was washed twice with PBST; HRP-labeled mouse anti-human Fab antibody was added and incubated at 37° C. for 40 min; the plate was washed three times with PBST and pat dry; 100 μl of TMB was added into each well, and placed in the dark at room temperature (20±5° C.) for 5 min; 50 μl of 2M $H_2SO_4$ stop solution was added to each well to stop the substrate reaction. OD value at 450 nm was read using a microplate reader. GraphPad Prism6 was used for data analysis, graphing and calculation of $EC_{50}$. The experimental results are shown in FIG. 3A. The $EC_{50}$s of anti-HER2/PD1 bispecific antibody-a, -b and positive control anti-HER2 monoclonal antibody binding to HER2 were 0.1975 nM, 0.2294 nM and 0.221 nM, respectively. The three have an equivalent affinity.

Figure 3B:
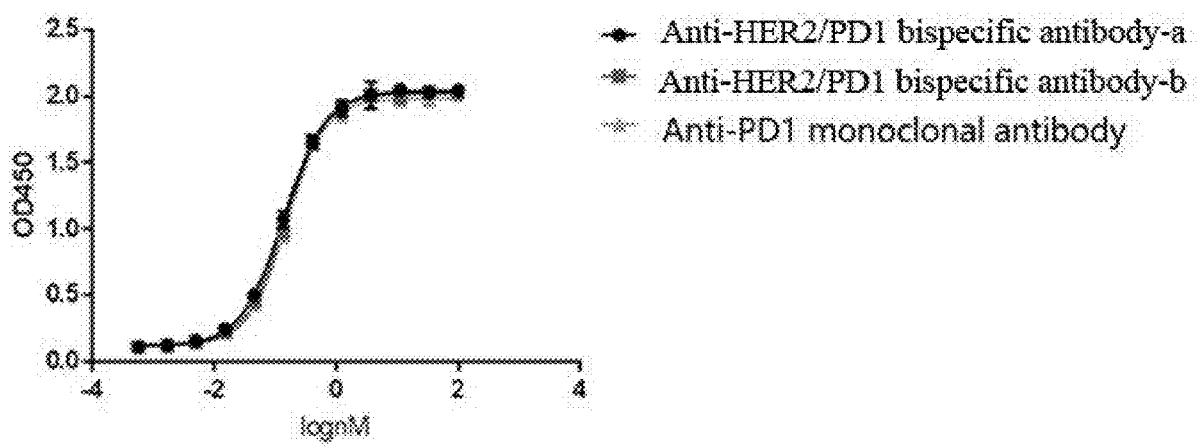
FIG. 3B: Binding of anti-HER2/PD1 bispecific antibody-a, -b to PD1-ECD detected by ELISA

In order to detect the binding ability of anti-HER2/PD1 bispecific antibody-a and -b to PD1, the recombinant PD1-ECD-hFc protein (prepared by Sunshine Guojian) was diluted to 200 ng/ml with PBS (pH7.4), added into an ELISA plate at 100 μl/well; incubated overnight at 4° C. The plate was washed twice with PBST; blocking solution (PBS+2% BSA) was added at 200 μl/well, placed at 37° C. for 1 hour, and then the plate was washed once for later use. The antibody to be tested was gradiently diluted with PBS+1% BSA, using anti-PD1 monoclonal antibody as positive control, with an initial concentration of 100 nM, gradually diluted 3-fold for a total of 12 gradients. They were added into the ELISA plate at 100 μl/well and placed at 37° C. for 1 h. The plate was washed twice with PBST; HRP-labeled mouse anti-human Fab antibody was added and incubated at 37° C. for 30 min; the plate was washed three times with PBST and pat dry, 100 μl of TMB was added into each well, and placed in the dark at room temperature (20±5° C.) for 5 min; 50 μl of 2M $H_2SO_4$ stop solution was added into each well to stop the substrate reaction. OD value at 450 nm was read using a microplate reader. GraphPad Prism6 was used for data analysis, graphing and calculation of $EC_{50}$. The experimental results are shown in FIG. 3B. The $EC_{50}$s of anti-HER2/PD1 bispecific antibody-a, -b and positive control anti-PD1 monoclonal antibody binding to PD1 were 0.1384 nM, 0.1525 nM and 0.1557 nM, respectively. The three have an equivalent affinity.

Figure 4A:
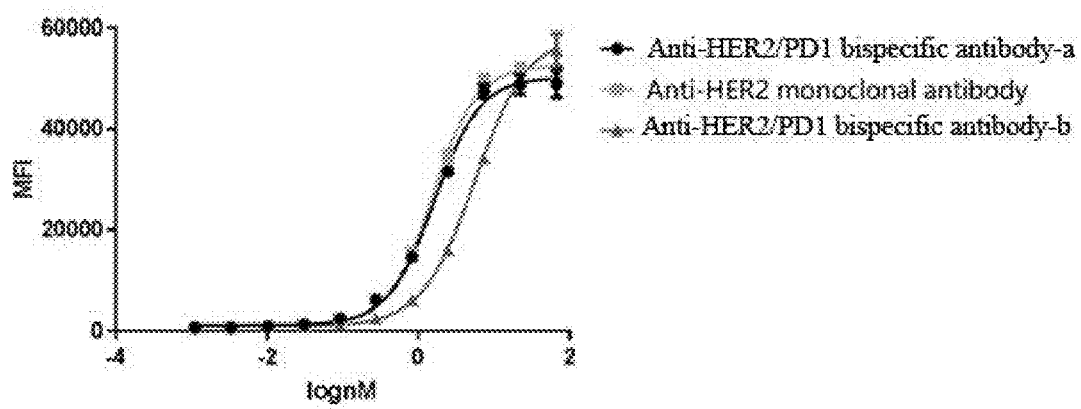
FIG. 4A: Binding of anti-HER2/PD1 bispecific antibody-a and anti-HER2/PD1 bispecific antibody-b to BT474 cells detected by FACS

Example 4. Detection of the Binding Affinity of Bispecific Antibody to Target Cells In this experiment, the human breast cancer cell BT474 with high expression of HER2 on the cell surface was used as the target cell, washed three times with PBS containing 0.5% BSA and centrifuged at 300 g for 5 min each time to discard the supernatant. The cells were resuspended in PBS containing 0.5% BSA to make the cell concentration $1\times10^6$ cells/mL, and added into a 96-well plate at 100 μL/well. Anti-HER2/PD1 bispecific antibody-a, -b and positive control anti-HER2 monoclonal antibody were diluted to 400 nM, and then gradually diluted for a total of 11 gradients, and added into a 96-well plate at 100 μL/well, mixed well with BT474 cells, and incubated at 4° C. for 1 hour. The cells were washed twice with PBS to remove unbound antibodies to be tested, and then incubated with 100 μl of 10 μg/ml goat anti-human IgG-FITC at 4° C. for 30 min, centrifuged at 300 g for 5 min, and washed with PBS twice to remove unbound secondary antibodies. Finally, the cells were resuspended in 200 μl PBS, and the binding affinity of the bispecific antibodies to the cells was determined by a Beckman Coulter CytoFLEX flow cytometer. The data obtained was fitted and analyzed by GraphPad Prism6 software. The experimental results are shown in FIG. 4A. Anti-HER2/PD1 bispecific antibody-a and anti-HER2/PD1 bispecific antibody-b can specifically bind to HER2 expressed on the cell surface. The experimental results are shown in FIG. 4A. The $EC_{50}$s of anti-HER2/PD1 bispecific antibody-a, -b and positive control anti-HER2 monoclonal antibody binding to BT474 cells were 1.64 nM, 5.669 nM, and 1.556 nM, respectively. Among them, anti-HER2/PD1 bispecific antibody-a and positive control HER2 monoclonal antibody have an equivalent affinity, while anti-HER2/PD1 bispecific antibody-b has a slightly weaker affinity compared to positive control anti-HER2 monoclonal antibody.

Figure 4B:
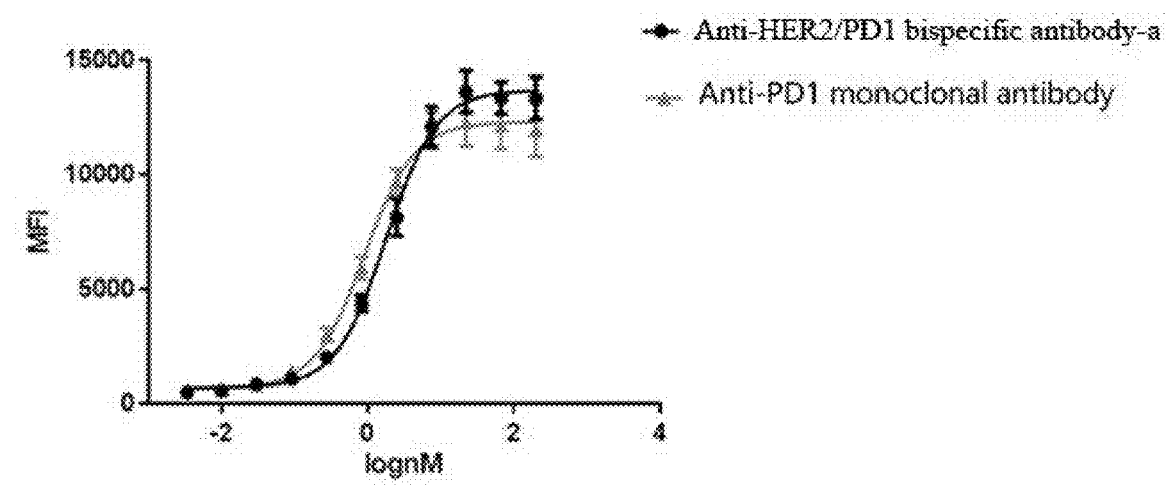
FIG. 4B: Binding of anti-HER2/PD1 bispecific antibody-a to PD1/CHO cells detected by FACS
Figure 4C:
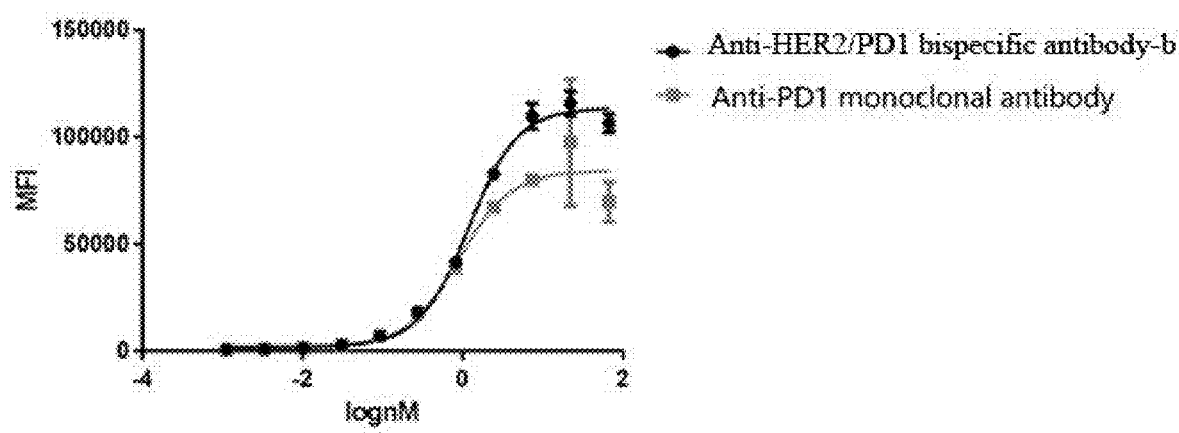
FIG. 4C: Binding of anti-HER2/PD1 bispecific antibody-b to PD1/CHO cells detected by FACS

Similarly, using CHO stable transfected cells expressing PD1 on the cell surface as target cells, the binding affinities of anti-HER2/PD1 bispecific antibody-a and anti-HER2/PD1 bispecific antibody-b to the cell were determined by flow cytometry. According to the same method as described above, the data obtained was fitted and analyzed by GraphPad Prism 6 software. The experimental results are shown in FIGS. 4B and 4C. Both anti-HER2/PD1 bispecific antibody-a and anti-HER2/PD1 bispecific antibody-b can specifically bind to PD1 expressed on the cell surface. The $EC_{50}$ of anti-HER2/PD1 bispecific antibody-a and positive control anti-PD1 monoclonal antibody were 1.777 nM and 0.8981 nM, respectively; the $EC_{50}$s of anti-HER2/PD1 bispecific antibody-b and positive control anti-PD1 monoclonal antibody were 1.192 nM and 0.8891 nM, respectively. The three have an equivalent affinity.

Example 5. Inhibition of Bispecific Antibody on the Proliferation of BT474 Cells In Vitro The human breast cancer cell line BT474 expresses the HER2 antigen molecule on its cell surface. Since BT474 cells, when cultured in vitro, their normal proliferation is partly dependent on the growth signal transmitted by HER2 receptor. Adding anti-HER2 antibody to the culture medium can inhibit the cell proliferation. Within a certain range, the concentration of antibody has a dose-effect relationship with the degree of cell proliferation inhibition. The degree of cell proliferation can be detected by CCK-8 (Cell Counting Kit-8) cell proliferation toxicity reagent. The dose-effect relationship curve is an inverse "S" curve.

Figure 5:
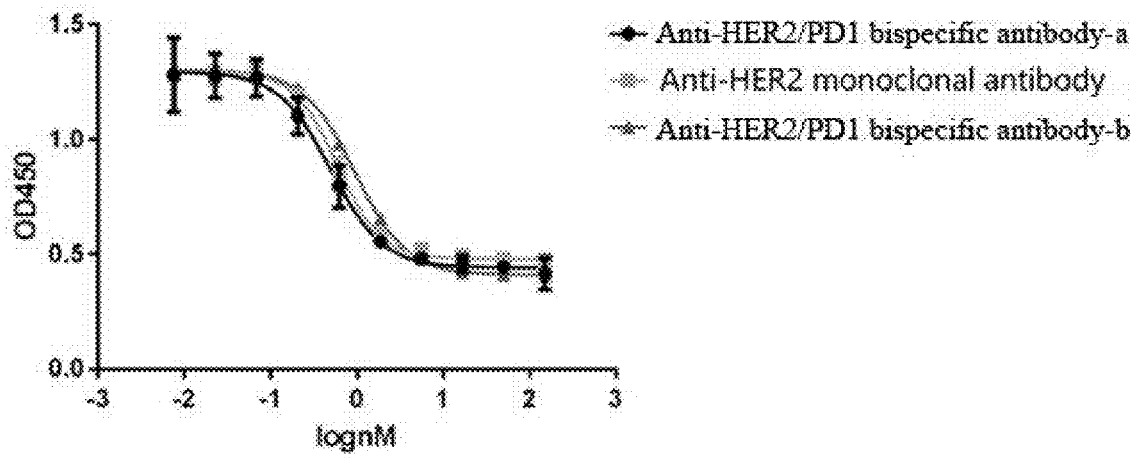
FIG. 5: Inhibition of anti-HER2/PD1 bispecific antibody-a and b on the proliferation of BT474 cells in vitro

BT474 cells were digested with trypsin, resuspended and then counted. According to the density of living cells, the cells were adjusted to a density of $5\times10^4$ cells/mL with complete medium, and added into Rows B~G of a 96-well cell culture plate at 100 μL/well. 200 μL/well of culture medium or PBS was added into the two Rows A and H to seal the edges. The cells were cultured adherently in a 37° C., 5% $CO_2$ incubator for 3 to 5 hours. Anti-HER2/PD1 bispecific antibodies-a and b and positive control anti-HER2 monoclonal antibody samples were prepared to be 300 nM solution using complete medium as diluent, and then gradually diluted 3-fold for a total of 11 gradients. The diluted samples were added to the corresponding cells in the 96-well plate and cultured in a 37° C., 5% $CO_2$ incubator for 7 days. Chromogenic solution was added into the cell culture plate at a ratio of 1:10 (sample dilution: CCK-8), and incubated in the $CO_2$ incubator for another 3-5 hours. OD value was measured using 650 nm as the reference wavelength and 450 nm as the detection wavelength. The data obtained was analyzed by GraphPad Prism 6 software. The experimental results are shown in FIG. 5. The $IC_{50}$ of anti-HER2/PD1 bispecific antibody-a, anti-HER2/PD1 bispecific antibody-b and positive control anti-HER2 monoclonal antibody were 0.4967 nM, 0.9427 nM, 0.5914 nM, respectively. The three have an equivalent inhibition rate.

Example 6. Activity of Bispecific Antibody to Blockade the Binding of PD1/PD-L1 at the Cellular Level The PD-L1 aAPC/CHO-K1 in logarithmic growth phase were digested with trypsin into single cells, transferred to a white, clear-bottom 96-well plate, 100 μL/well, 40,000 cells/well, incubated at 37° C., 5% $CO_2$ overnight. Anti-HER2/PD1 bispecific antibody-a, -b, anti-PD1 monoclonal antibody, and isotype negative control sample were gradually diluted 3-fold to 2× working solution concentration from an initial concentration of 600 nM. The PD1 effector cells with a density of $1.4-2\times10^6$ cells/mL and a cell viability above 95% were diluted with assay buffer to produce a single cell suspension of $1.25\times10^6$ cells/ml.

The supernatant of PD-L1 aAPC/CHO-K1 cells that had been seeded the day before was discarded, and 40 μl of gradually diluted bispecific antibody/PD1 monoclonal antibody working solution was added; then an equal volume of PD1 effector cells was added, incubated at 37° C., 5% $CO_2$ for 6 hours. 80 μl of Bio-Glo detection reagent was added into each well, incubated at room temperature for 10 min, and luminescence was read with spectramax i3.

Figure 6A:
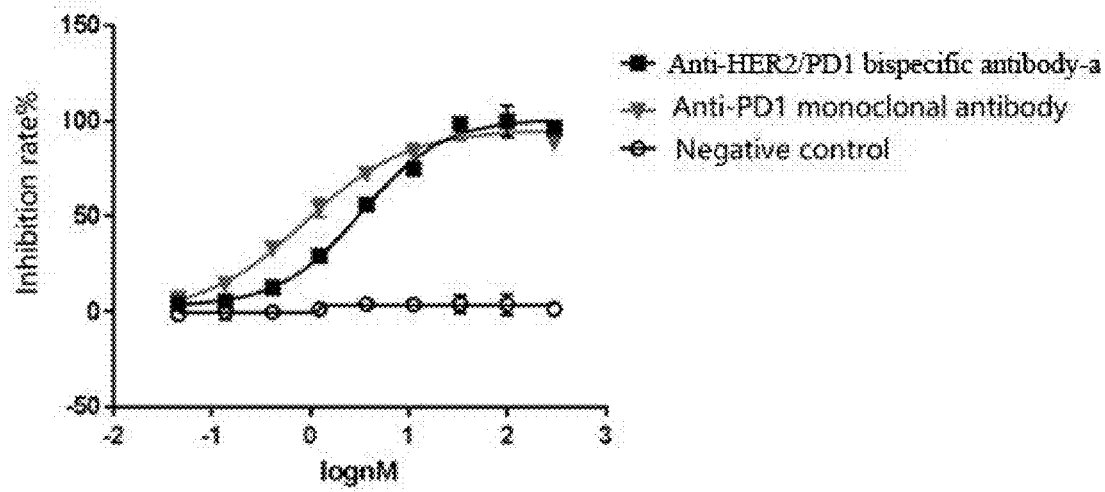
FIG. 6A: Activity of anti-HER2/PD1 bispecific antibody-a to blockade PD1/PD-L1 binding at cellular level
Figure 6B:
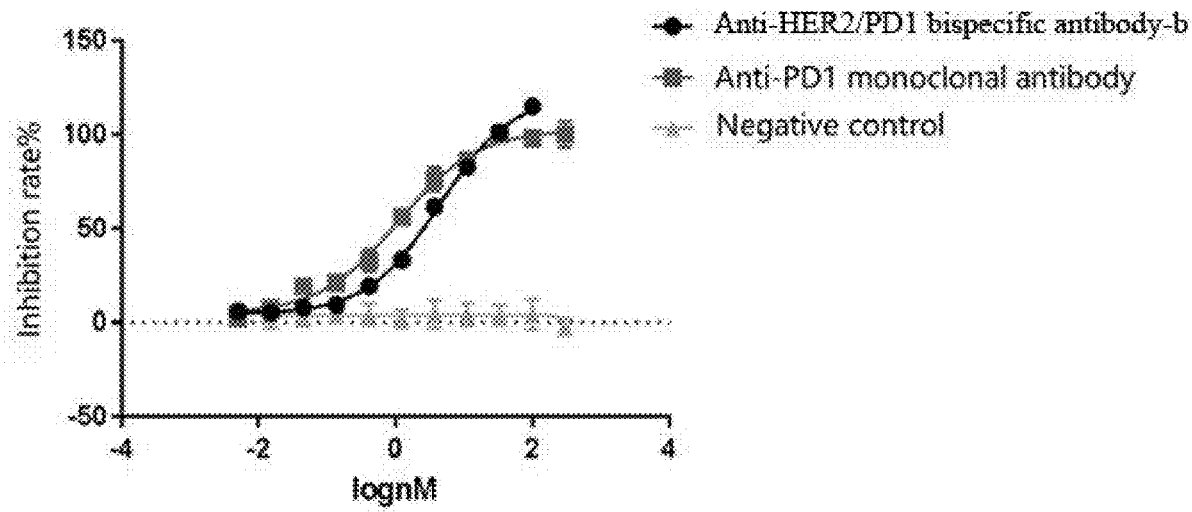
FIG. 6B: Activity of anti-HER2/PD1 bispecific antibody-b to blockade PD1/PD-L1 binding at cellular level

All data were from two replicate wells. The obtained signal values were averaged and then fitted with 4-parameter method to draw the curve, as shown in FIGS. 6A, 6B, and to obtain the data of $IC_{50}$, top, bottom, hillslope and etc. of anti-HER2/PD1 bispecific antibody-a, as shown in Table 1:

TABLE 1

| | Anti-HER2/PD1 bispecific antibody-a | Anti-PD1 monoclonal antibody |
|---|---|---|
| Bottom | 2.707 | −1.048 |
| Top | 101.1 | 95.61 |
| lgIC$_{50}$ | 0.5161 | −0.05017 |
| Hill Slope | 1.048 | 0.8425 |
| IC$_{50}$ | 3.282 | 0.8909 |

The data of $IC_{50}$, top, bottom, hillslope and etc. of anti-HER2/PD1 bispecific antibody-b are shown in table 2.

TABLE 2

|  | Anti-HER2/PD1 bispecific antibody-b | Anti-PD1 monoclonal antibody |
|---|---|---|
| Bottom | 4.435 | 4.39 |
| Top | 121.3 | 102.8 |
| lgIC$_{50}$ | 0.6467 | 0.03983 |
| Hill Slope | 0.8171 | 0.7548 |
| IC$_{50}$ | 4.433 | 1.096 |

Example 7. Affinity of Bispecific Antibody to Antigen Determined by Biacore™ 8K

The kinetic parameters of the binding between the bispecific antibody—and the antigen HER2-ECD-his were determined by the proteinA capture method. The bispecific antibody with a concentration of 1 μg/ml was bound to the Protein A chip, and the antigen HER2-ECD-his was serially diluted 2-fold from 50 nM with 1×HBS-EP working solution, and 6 concentration gradients were provided to bind to the antibody, and dissociated in HBS-EP working solution.

The kinetic parameters of the binding between the bispecific antibody—and the antigen PD1-ECD-his were determined by the proteinA capture method. The bispecific antibody with a concentration of 1 μg/ml was bound to the Protein A chip, and the antigen PD1-ECD-his was serially diluted 2-fold from 250 nM with 1×HBS-EP working solution, and 5 concentration gradients were provided to bind to the antibody, and dissociated in HBS-EP working solution.

The kinetic parameters of the binding of anti-HER2/PD1 bispecific antibody-a to HER2-ECD-His and PD1-ECD-his are shown in Table 3. The results show that anti-HER2/PD1 bispecific antibody-a has good affinity for antigens PD1 and HER2.

TABLE 3

| Analyte Solution | ka (1/Ms) | kd (1/s) | KD (M) |
|---|---|---|---|
| PD1-ECD-his | 2.43E+04 | 8.57E−05 | 3.53E−09 |
| HER2-ECD-his | 5.88E+04 | 1.92E−04 | 3.27E−09 |

KD is the affinity constant; ka is the antigen-antibody binding rate; kd is the antigen-antibody dissociation rate; KD=kd/ka.

The kinetic parameters of the binding of anti-HER2/PD1 bispecific antibody-b to HER2-ECD-His and PD1-ECD-his are shown in Table 4. The results show that anti-HER2/PD1 bispecific antibody-b has good affinity for antigens PD1 and HER2.

TABLE 4

| Kinetic parameters of anti-HER2/PD1 bispecific antibody-b | | | |
|---|---|---|---|
| Analyte Solution | ka (1/Ms) | kd (1/s) | KD (M) |
| PD1-ECD-his | 3.85E+04 | 1.86E−04 | 4.83E−09 |
| HER2-ECD-his | 2.16E+05 | 1.71E−04 | 7.92E−10 |

KD is the affinity constant; ka is the antigen-antibody binding rate; kd is the antigen-antibody dissociation rate; KD=kd/ka.

Example 8. Pharmacokinetic Study of Anti-HER2/PD1 Bispecific Antibody-a and Anti-HER2/PD1 Bispecific Antibody-b Four SD rats from each group, weighing about 200 g were injected with a dose of 2 mg of antibody by the tail vein, respectively. The blood was collected from the orbit at a specific time after treatment, and after natural coagulation, the blood was centrifuged at 8000 rpm/min to collect the serum.

The serum drug concentration of anti-HER2/PD1 bispecific antibody-a was detected by the following method:

1) Two ELISA plates were coated with 50 ng/well of HER2-His overnight at 4° C. The next day, the plates were washed twice with PBST, and then blocked with PBS+2% BSA at 37° C. for 2 hours. The standard of anti-HER2/PD1 bispecific antibody-a was diluted two-fold from an initial concentration of 0.5 μg/mL into 12 gradients. Each serum sample was diluted 2000 times. The above samples were added into the blocked ELISA plates, incubated at 37° C. for one hour. Then, the plates were washed twice with PBST.

Detection of anti-HER2 antibody: HRP-labeled mouse anti-human Fab antibody was added to one of the plates, diluted 1:3000, 100 μL/well, incubated at 37° C. for 40 min. The plate was washed 4 times with PBST and pat dry. 100 μl of TMB was added into each well, placed in the dark at room temperature (20±5° C.) for 5 min; 50 μl of 2M $H_2SO_4$ stop solution was added into each well to stop the substrate reaction. OD value at 450 nm was read using a microplate reader.

Detection of anti-PD1 antibody: Biotinylated PD1-hFc was added into another plate, 7.5 ng/well, incubated for 1 hour. The plate was washed, added with Streptavidin-HRP, diluted 1:1000, placed at 37° C. for 30 min. The plate was washed 4 times with PBST and pat dry. 100 μl of TMB was added into each well, placed in the dark at room temperature (20±5° C.) for 5 min; 50 μl of 2M $H_2SO_4$ stop solution was added into each well to stop the substrate reaction. OD value at 450 nm was read using a microplate reader.

2) An ELISA plate was coated with ProteinA to detect the Fab fragment of the antibody, 100 ng/well, overnight at 4° C.; the next day, the plate was washed twice with PBST, and then blocked with PBS+2% BSA at 37° C. for 2 hours. The plate was washed twice with PBST. The standard of anti-HER2/PD1 bispecific antibody-a was diluted two-fold from an initial concentration of 1000 ng/mL into 12 gradients. The rat serum samples were diluted 2000 times. The above two groups of samples were added into the blocked ELISA plate and incubated for 1 hour; the plate was washed twice with PBST; HRP-labeled mouse anti-human Fab antibody was added, and placed at 37° C. for 30 min; the plate was washed three times with PBST, pat dry; 100 μl of TMB was added into each well, and placed in the dark at room temperature (20±5° C.) for 5 min; 50 μl of 2M $H_2SO_4$ stop solution was added into each well to stop the substrate reaction. OD value at 450 nm was read using a microplate reader.

Figure 7A:
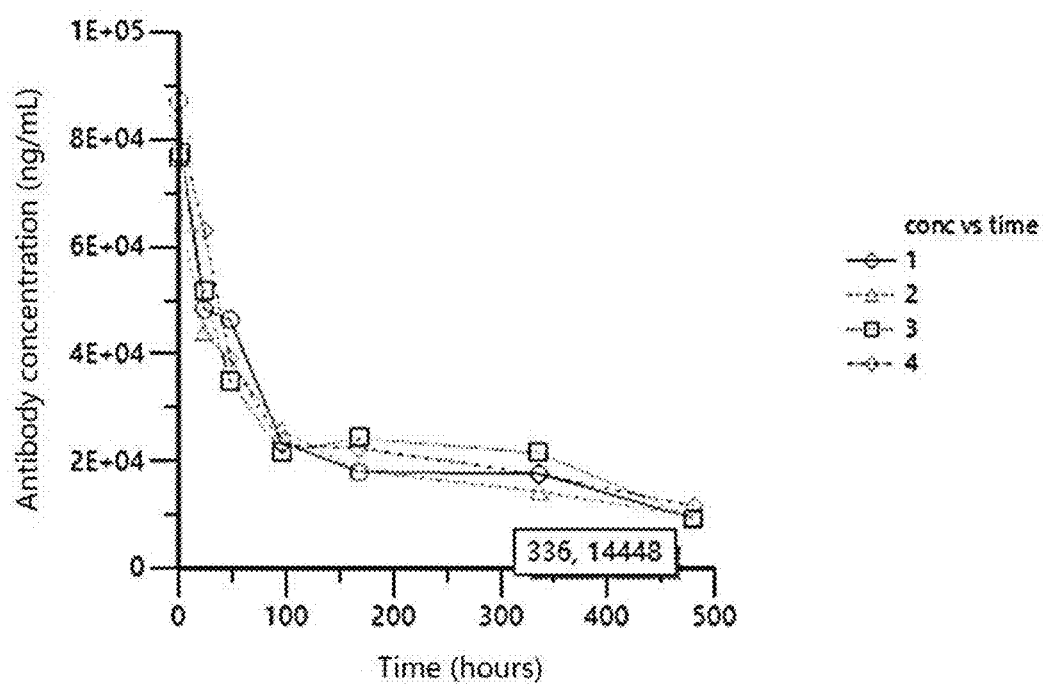
FIG. 7A: Detection of the half-life of anti-HER2 antibody in anti-HER2/PD1 bispecific antibody-a
Figure 7B:
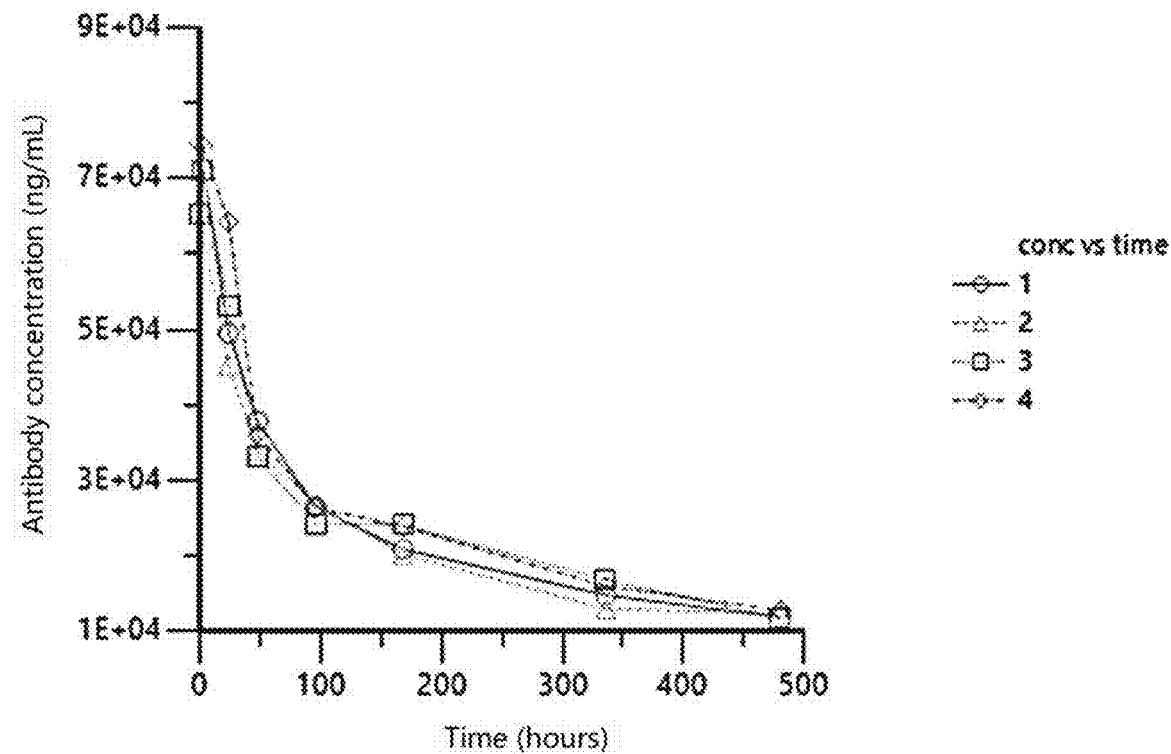
FIG. 7B: Detection of the half-life of anti-HER2/PD1 bispecific antibody-a with biotinylated PD1
Figure 7C:
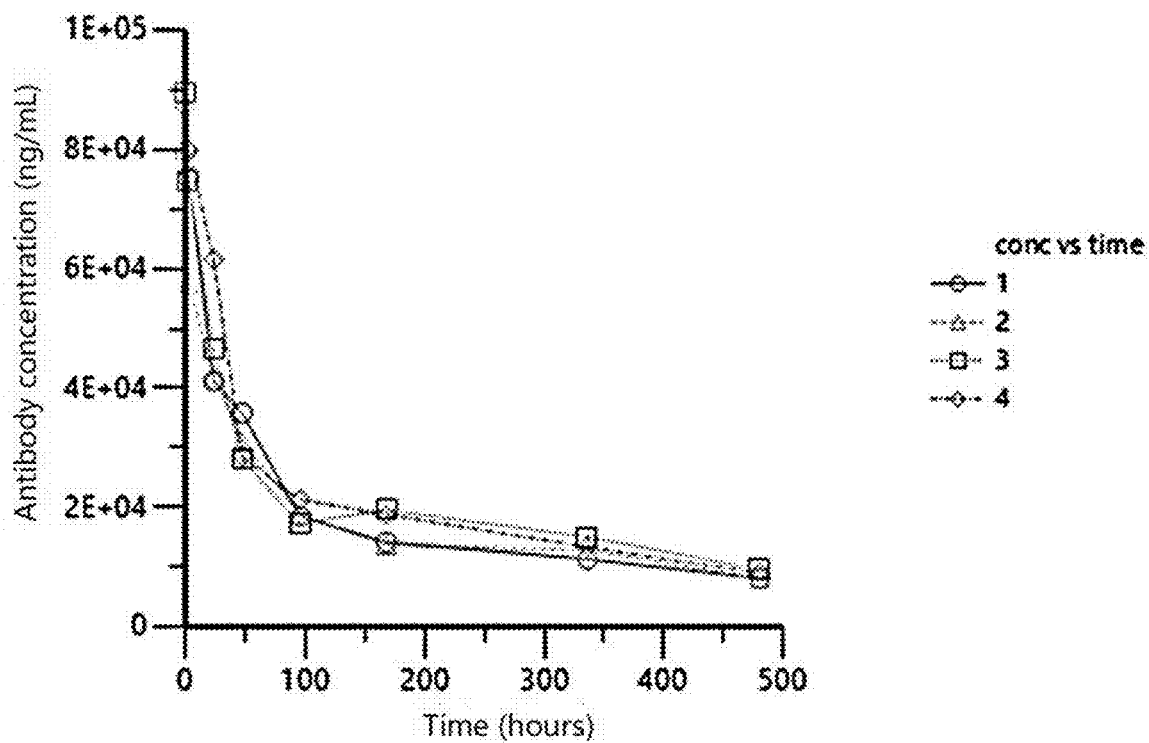
FIG. 7C: Detection of the half-life of anti-HER2/PD1 bispecific antibody-a with proteinA

Phoenix software was used to calculate the half-life of the antibody drug in rats, and GraphPad Prism6 was used for data analysis and graphing. The pharmacokinetic parameters are shown in Tables 5, 6, and 7, and the experimental results are shown in FIGS. 7A, 7B, and 7C. The half-lives in rats detected by the two methods were: 273 hours for the anti-HER2 antibody, 333 hours for the anti-PD1 antibody according to the first method; the half-life was 333 hours according to the second method. The three sets of data were similar, and it can be inferred that the half-life of anti-HER2/PD1 bispecific antibody-a is about 300 hours.

The half-life of the anti-HER2 antibody is shown in Table 5:

TABLE 5

| Group | HL_Lambda_z (hr) |
|---|---|
| 1 | 217.1994 |
| 2 | 296.66456 |
| 3 | 245.3652 |
| 4 | 333.21473 |
| Average | 273 |

The half-life of anti-HER2/PD1 bispecific antibody-a detected with biotinylated PD1 is shown in Table 6:

TABLE 6

| Group | HL_Lambda_z(hr) |
|---|---|
| 1 | 382.77325 |
| 2 | 294.69571 |
| 3 | 302.13064 |
| 4 | 353.0152 |
| Average | 333 |

The half-life of anti-HER2/PD1 bispecific antibody-a detected with proteinA is shown in Table 7:

TABLE 7

| Group | HL_Lambda_z(hr) |
|---|---|
| 1 | 346.75496 |
| 2 | 369.60234 |
| 3 | 306.45773 |
| 4 | 310.91707 |
| Average | 333 |

The serum drug concentration of anti-HER2/PD1 bispecific antibody-b was detected by the following method:

1) Detection of anti-HER2 antibody: An ELISA plate was coated with 50 ng/well of HER2-His overnight at 4° C. The next day, the plate was washed twice with PBST, and then blocked with PBS+2% BSA at 37° C. for 2 hours. The standard of anti-HER2/PD1 bispecific antibody-b was diluted two-fold from an initial concentration of 0.5 μg/mL into 12 gradients. Each serum sample was diluted 2000 times, added into the blocked ELISA plate, incubated at 37° C. for one hour. Then, the plate was washed twice with PBST. HRP-labeled mouse anti-human Fab antibody was added, diluted 1:3000, 100 μL/well, incubated at 37° C. for 40 min. The plate was washed 4 times with PBST and pat dry. 100 μl of TMB was added into each well, placed in the dark at room temperature (20±5° C.) for 5 min; 50 μl of 2M $H_2SO_4$ stop solution was added into each well to stop the substrate reaction. OD value at 450 nm was read using a microplate reader.

2) Detection of anti-PD1 antibody: An ELISA plate was coated with PD1-ECD-hFc, 20 ng/well. The methods of coating, washing plate, and diluting the standard were the same as above. The serum samples were diluted 1000-2000 times and added into the blocked ELISA plate, incubated at 37° C. for 1 hour. Then the plate was washed twice with PBST. HRP-labeled mouse anti-human Fab antibody was added, diluted 1:3000, 100 μL/well, incubated at 37° C. for 40 min. The plate was washed 4 times with PBST and pat dry. 100 μl of TMB was added into each well, placed in the dark at room temperature (20±5° C.) for 5 min; 50 μl of 2M $H_2SO_4$ stop solution was added into each well to stop the substrate reaction. OD value at 450 nm was read using a microplate reader.

3) An ELISA plate was coated with ProteinA, 100 ng/well, overnight at 4° C., to detect the Fab fragment of the antibody; the next day, the plate was washed twice with PBST, and then blocked with PBS+2% BSA at 37° C. for 2 hours. The plate was washed twice with PBST. The standard of anti-HER-2/PD1 bispecific antibody-b was diluted two-fold from an initial concentration of 1000 ng/mL into 12 gradients. The rat serum samples were diluted 500-1000 times, added into the blocked ELISA plate and incubated for 1 hour; the plate was washed twice with PBST; HRP-labeled mouse anti-human Fab antibody was added, and placed at 37° C. for 30 min; the plate was washed 4 times, and pat dry. 100 μl of TMB was added into each well, and placed in the dark at room temperature (20±5° C.) for 5 min; 50 μl of 2M $H_2SO_4$ stop solution was added into each well to stop the substrate reaction. OD value at 450 nm was read using a microplate reader.

Figure 7D:
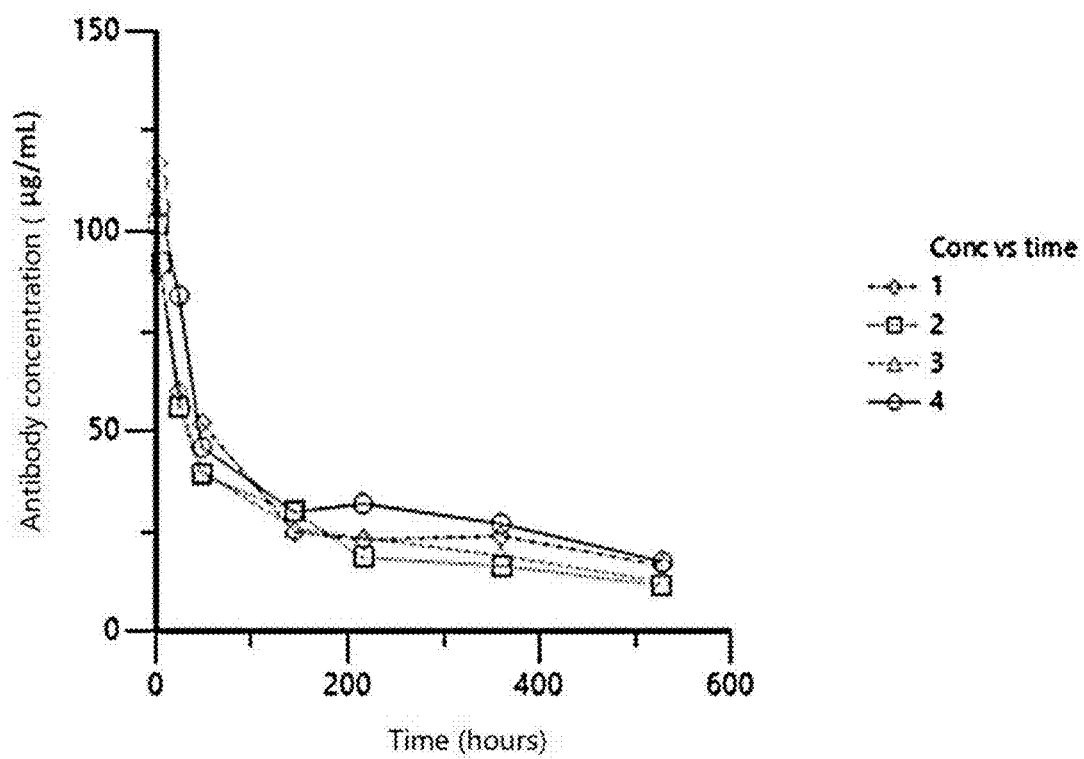
FIG. 7D: Detection of the half-life of anti-HER2 antibody in anti-HER2/PD1 bispecific antibody-b
Figure 7E:
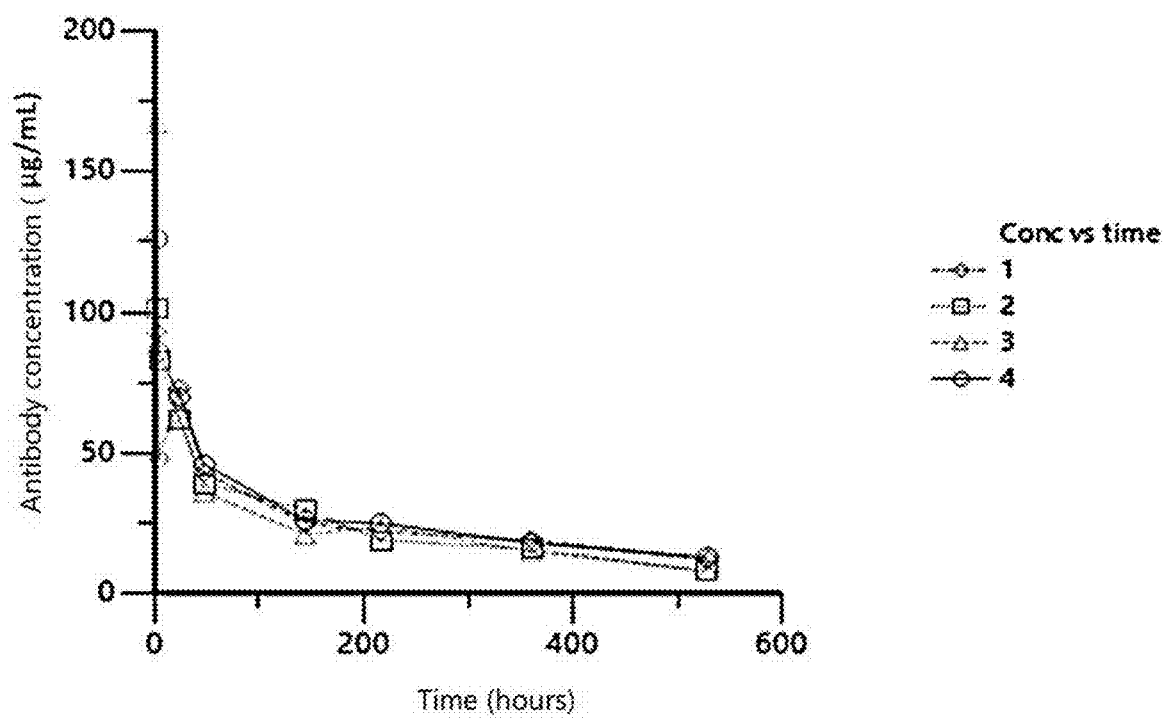
FIG. 7E: Detection of the half-life of anti-PD1 antibody in anti-HER2/PD1 bispecific antibody-b
Figure 7F:
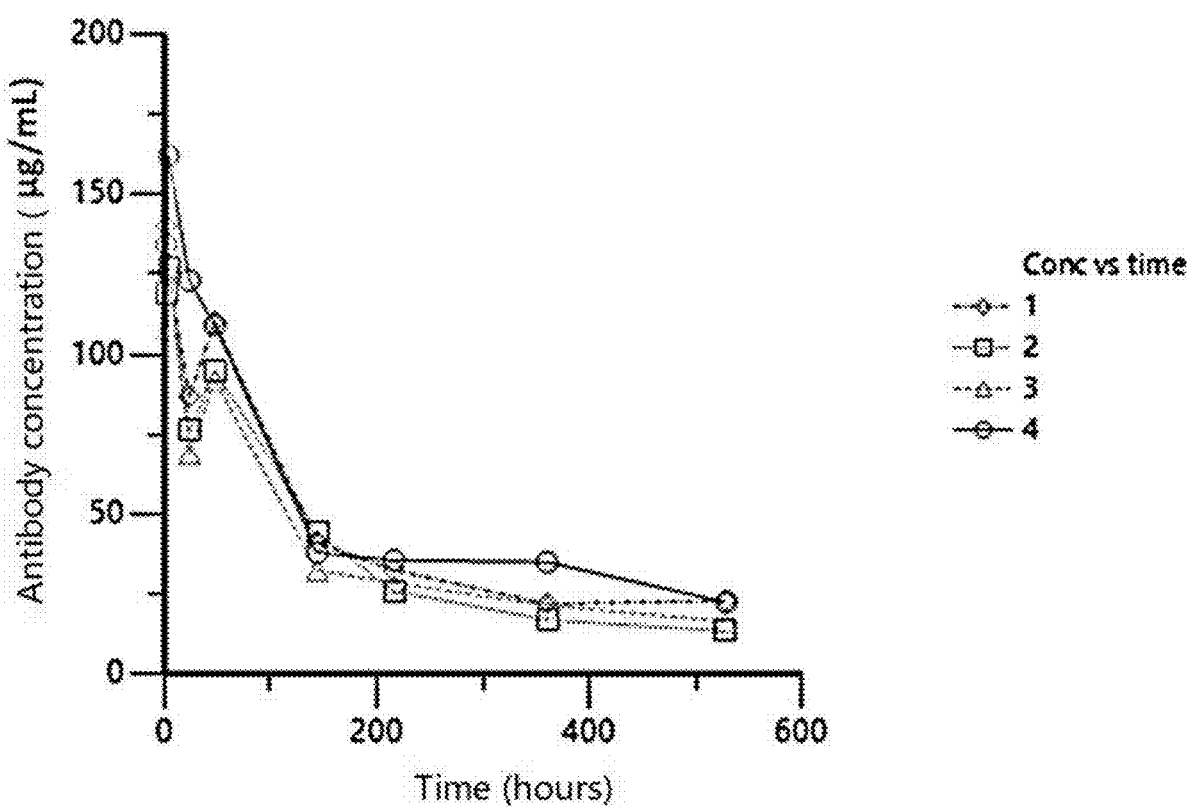
FIG. 7F: Detection of the half-life of anti-HER2/PD1 bispecific antibody-a with proteinA

Phoenix software was used to calculate the half-life of the antibody drug in rats, and GraphPad Prism6 was used for data analysis and graphing. The pharmacokinetic parameters are shown in Tables 8, 9, and 10, and the experimental results are shown in FIGS. 7D, 7E, and 7F. The half-lives in rats detected by the three methods were: 312 hours according to the first method; 280 hours according to the second method, and 277 hours according to the third hours. The three sets of data were similar, and it can be inferred that the half-life of anti-HER2/PD1 bispecific antibody-b is about 280 hours.

The detected half-life of the anti-HER2 antibody is shown in Table 8:

TABLE 8

| Group | HL_Lambda_z(hr) |
|---|---|
| 1 | 249.10194 |
| 2 | 279.51118 |
| 3 | 366.19333 |
| 4 | 355.05384 |
| Average | 312 |

The detected half-life of the anti-PD1 antibody is shown in Table 9:

TABLE 9

| Group | HL_Lambda_z(hr) |
|---|---|
| 1 | 375.61812 |
| 2 | 216.88057 |
| 3 | 196.51091 |
| 4 | 331.40524 |
| Average | 280 |

The half-life of anti-HER2/PD1 bispecific antibody-b detected by protein A is shown in Table 10:

TABLE 10

| Group | HL_Lambda_z(hr) |
|---|---|
| 1 | 189.38172 |
| 2 | 333.14994 |
| 3 | 389.77667 |
| 4 | 196.6228 |
| Average | 277 |

Example 9. ADCC Effect of Anti-HER2/PD1 Bispecific Antibody-a

Because the HER2/PD1 bispecific antibody can not only bind to tumor cells expressing HER2, and bind to T cells expressing PD-1, the Fc segment of the antibody can also bind to NK cells.

On the one hand, this experiment detects whether NK92a cells can kill CD4+ T cells bound to the antibody; on the other hand, it detects whether NK92a cells kill BT474 tumor cells bound to the antibody.

1) Whether NK92a cells have a killing effect on CD4+ T cells: Activated T cells express PD1, which can be bound by the anti-HER2/PD1 bispecific antibody-a. Fc segment of anti-HER2/PD1 bispecific antibody-a can bind to Fc receptor of the effector cells NK, and the addition of NK cells can detect whether T cells are killed.

The experimental methods were as follows:

Activation of CD4+ T cells: Anti-CD3 antibody was prepared with D-PBS into a concentration of 5 μg/mL, and used to coat a 24-well cell culture plate overnight at 4° C. The next day, $5 \times 10^5$ CD4+ T cells were added into each well, and 2 μg/mL of anti-CD28 antibody and 100 U/mL of IL2 were added at the same time, placed in a 37° C., $CO_2$ incubator, and activated for 72 h.

The activated T cells were collected, and the expression of PD1 was detected by FACS. Then, the T cells with high expression of PD1 were prepared with 1640 medium containing 5% FBS into $2 \times 10^5$ cells/mL, and added into a 96-well plate, 50 μL/well.

Dilution of anti-HER2/PD1 bispecific antibody-a and the negative control sample HER2 monoclonal antibody: anti-HER2/PD1 bispecific antibody-a and anti-HER2 monoclonal antibody were prepared into an initial concentration of 400 nM, and subjected to serial 5-fold dilution, and then added into a 96 well plate paved with T cells, incubated in a 37° C., $CO_2$ incubator for 15 min. During this period, NK92a cells were adjusted to $5 \times 10^5$ cells/mL with 1640 medium containing 5% FBS, and added into the above 96-well plate at 100 μL/well, incubated in a 37° C., $CO_2$ incubator for 3 hours.

Figure 8A:
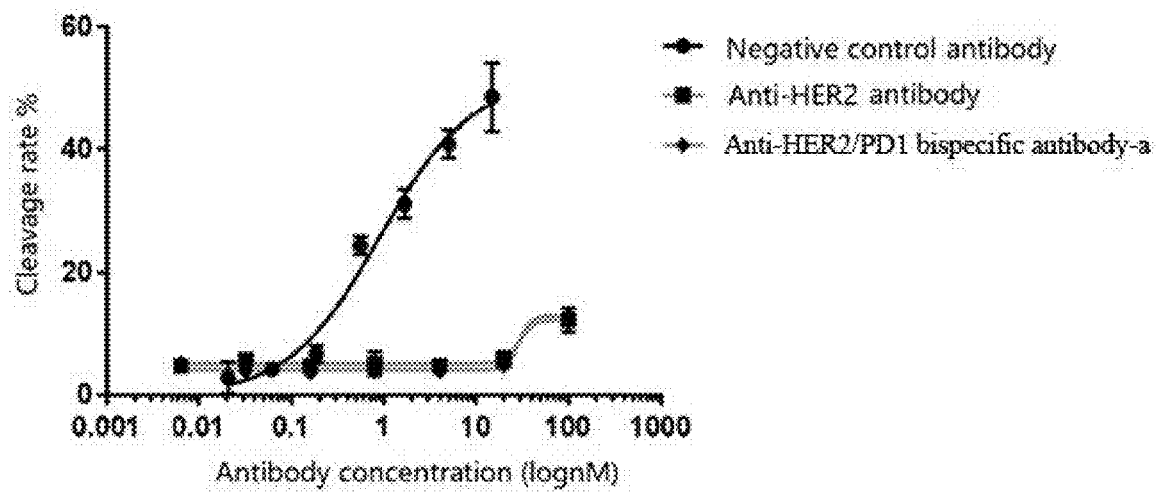
FIG. 8A: ADCC towards CD4+ T cells

The 96-well plate was centrifuged at 300 g for 5 min, the supernatant was transferred and centrifuged once again. 100 μL of the supernatant was transferred to another 96-well plate. LDH substrate was added at 50 μL/well and incubated for 15 min. SpectraMaxM5 microplate reader was used to read the values using 450 nm as the detection wavelength and 650 nm as the reference wavelength, and GraphPad Prism6 was used for data analysis and graphing. As shown in FIG. 8A, NK92a cells have no obvious killing effect on CD4+ T cells, and have only a weak killing effect at high concentrations of anti-HER2/PD1 bispecific antibody-a.

2) ADCC Towards BT474 Tumor Cells

The HER2 antigen is expressed on the surface of BT474 cells, which can be combined by the added anti-HER2/PD1 bispecific antibody-a. The Fc segment of anti-HER2/PD1 bispecific antibody-a binds to the Fc receptor of effector cells NK, and the addition of NK cells can detect whether BT474 cells are killed.

The experimental methods were as follows:

BT474 cells were diluted with 1640 medium containing 5% FBS to $2 \times 10^5$ cells/mL, added into a 96-well flat bottom plate, 50 μL/well, and placed in a 37° C., 5% $CO_2$ incubator overnight.

Dilution of anti-HER2/PD1 bispecific antibody-a and the negative control sample HER2 monoclonal antibody: anti-HER2/PD1 bispecific antibody-a and HER2 monoclonal antibody were prepared into an initial concentration of 200 nM, and subjected to gradual 4-fold dilution, and then added into a 96 well plate paved with BT474 cells, incubated in a 37° C., $CO_2$ incubator for 15 min. During this period, NK92a cells were adjusted to $5 \times 10^5$ cells/mL with 1640 medium containing 5% FBS, and added into the above 96-well plate at 100 μL/well, incubated in a 37° C., $CO_2$ incubator for 3 hours.

Figure 8B:
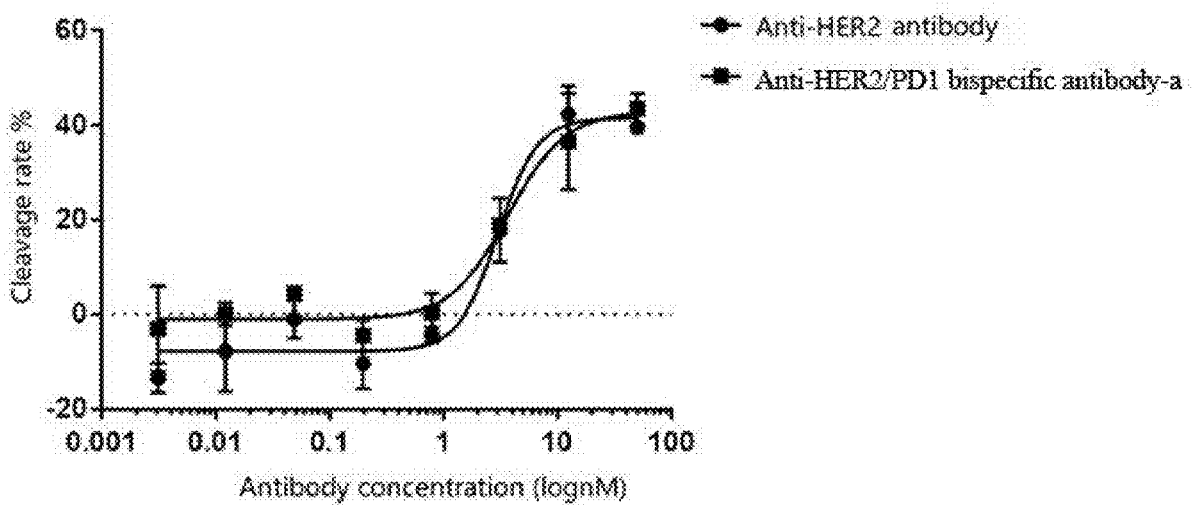
FIG. 8B: ADCC towards BT474 tumor cells

The 96-well plate was centrifuged at 300 g for 5 min, the supernatant was transferred and centrifuged once again. 100 μL of the supernatant was transferred to another 96-well plate. LDH substrate was added at 50 μL/well and incubated for 15 min. SpectraMaxM5 microplate reader was used to read the values using 450 nm as the detection wavelength and 650 nm as the reference wavelength, and GraphPad Prism6 was used for data analysis and graphing. As shown in FIG. 8B, NK92a cells have significant killing effect on BT474 tumor cells, which is similar to the anti-HER2 monoclonal antibody.

Example 10. Detection of the Synergistic Effect of Anti-HER2/PD1 Bispecific Antibody-a at the Cellular Level To detect the synergistic effect of the two targets of anti-HER2/PD1 bispecific antibody—at the cellular level, the following conditions must be met: HER2 antigen is expressed on tumor cells, and the proliferation of tumor cells can be inhibited by HER2 antibody; meanwhile, PD-L1 is expressed, which can bind to PD-1 on T cells, so the addition of anti-PD1 antibody blockade the PD-1/PD-L1 binding, releases the suppression of T cells, and plays a role in killing tumors. Since no cell strain meeting these conditions was screened, a lentiviral transfection method was used to recombine the PD-L1 gene into the human gastric cancer cell strain NCI-N87. PD-L1 was highly expressed on the cell surface of the constructed N87-PDL1 cells, detected by FACS.

Figure 9A:
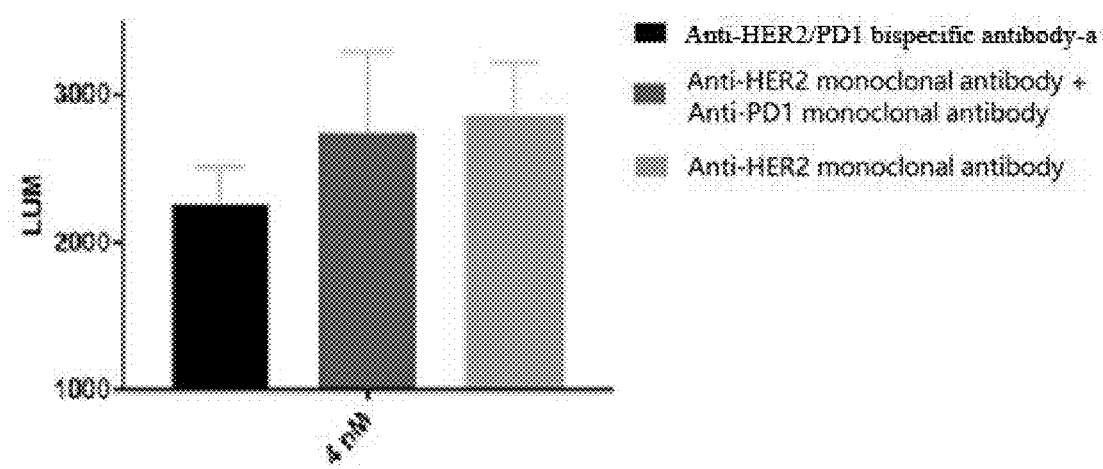
FIG. 9A: Synergistic killing effect of anti-HER2/PD1 bispecific antibody-a on N87-PDL1 cells
Figure 9B:
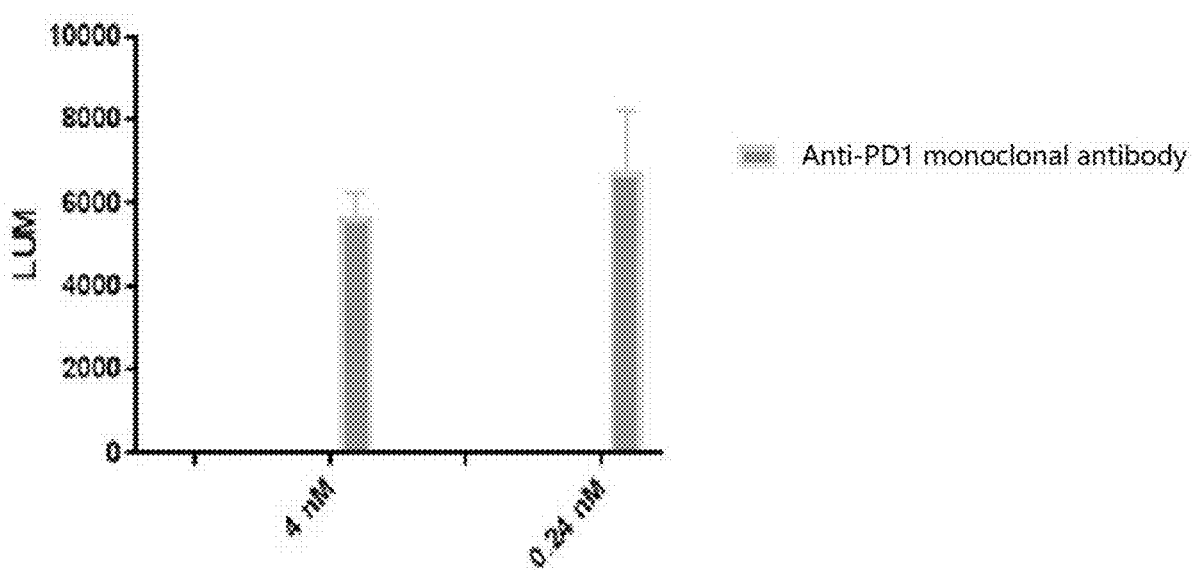
FIG. 9B: Effect of PD1 control monoclonal antibody on N87-PDL1 cells

N87-PDL1 cells in the logarithmic growth phase were digested with trypsin, diluted to $1 \times 10^5$/mL in 1640 medium supplemented with 1% FBS, and transferred to a white, clear-bottom 96-well plate, incubated at 37° C., 5% $CO_2$ overnight. The next day, the antibody to be tested and fresh PBMC cells were added, 50 μL/well. The antibodies were antiHER2/PD1 bispecific antibody-a, anti-HER2 monoclonal antibody, anti-HER2 monoclonal antibody plus anti-PD1 monoclonal antibody, and anti-PD1 monoclonal antibody, at a concentration of 4 nM. PBMC was diluted in 1640 medium supplemented with 1% FBS, at $10^5$/well, incubated at 37° C. and 5% $CO_2$ for another 6 days. Then the plate was washed three times with PBS, CellTiter-Glo was diluted 1:1 with medium, and added into the 96-well plate at 100 μL/well. Luminescence was read using spectramax i3. GraphPad Prism was used for data analysis and graphing, see FIGS. 9A and 9B. The data show that anti-HER2/PD1 bispecific antibody-a is more effective than anti-HER2 monoclonal antibody in killing tumors, and better than anti-HER2 monoclonal antibody plus anti-PD1 monoclonal antibody, indicating that the bispecificantibody has a synergistic anti-tumor effect.

Example 11. Anti-Tumor Effect of Anti-HER2/PD1 Bispecific-Antibody-a on NCI-N87 Xenograft Model Human gastric cancer cell strain NCI-N87 cells cultured in vitro were collected, and adjusted to a cell concentration of 5×10⁷ cells/mL, resuspended in serum-free medium. Under aseptic conditions, 100 μL of cell suspension was inoculated subcutaneously into the back of nude mice. The length and width of the xenografts were measured with a vernier caliper, to calculate the tumor volume. The animals were randomly divided into groups after the tumor volume grew to 100-200 mm³.

The dose of the tested sample anti-HER2/PD1 bispecific antibody-a was divided into two groups, 20 mg/kg, 4 mg/kg, i.e., 0.4 mg/mouse, 0.08 mg/mouse, and the dose of positive control drug anti-HER2 monoclonal antibody was 15 mg/kg, i.e., 0.3 mg/mouse. The control group was given the same volume of PBS. The administration route was intraperitoneal administration, with an administration volume of 0.2 mL/mouse (20 g), twice a week for three consecutive weeks.

Figure 10:
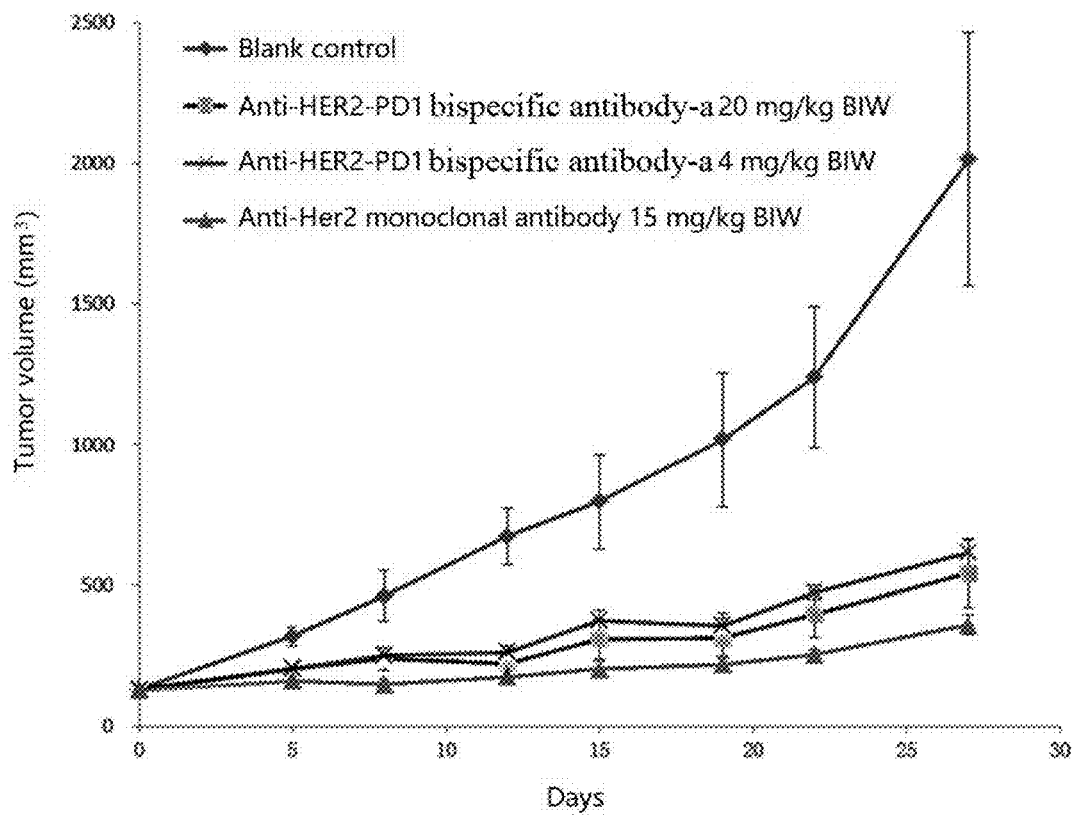
FIG. 10: Anti-tumor effect of anti-HER2/PD1 bispecific antibody-a on NCI-N87 xenograft model

The xenograft volume was measured twice a week, and the mice were weighed and recorded. Tumor volume (TV) was calculated by the formula: TV=½×length×width². Relative tumor volume (RTV) was calculated according to the measurement results by the calculation formula: RTV=Vt/V0. Wherein V0 is the tumor volume measured at the beginning of the administration (i.e., d0), and Vt is the tumor volume measured at each time. The evaluation index of anti-tumor activity is the relative tumor proliferation rate T/C (%), which is calculated by the formula: T/C (%)= (TRTV/CRTV)×100 (TRTV: treatment group RTV; CRTV: negative control group RTV); Tumor inhibition rate=1−T/C (%). Evaluation standard for efficacy: it is ineffective if T/C (%)>40%; it is effective if T/C (%)≤40% and p≤0.05 by statistics analysis. The results of the experiment are shown in FIG. 10. Anti-HER2/PD1 bispecific antibody-a is similar to positive control HER2 monoclonal antibody.

Figure 11:
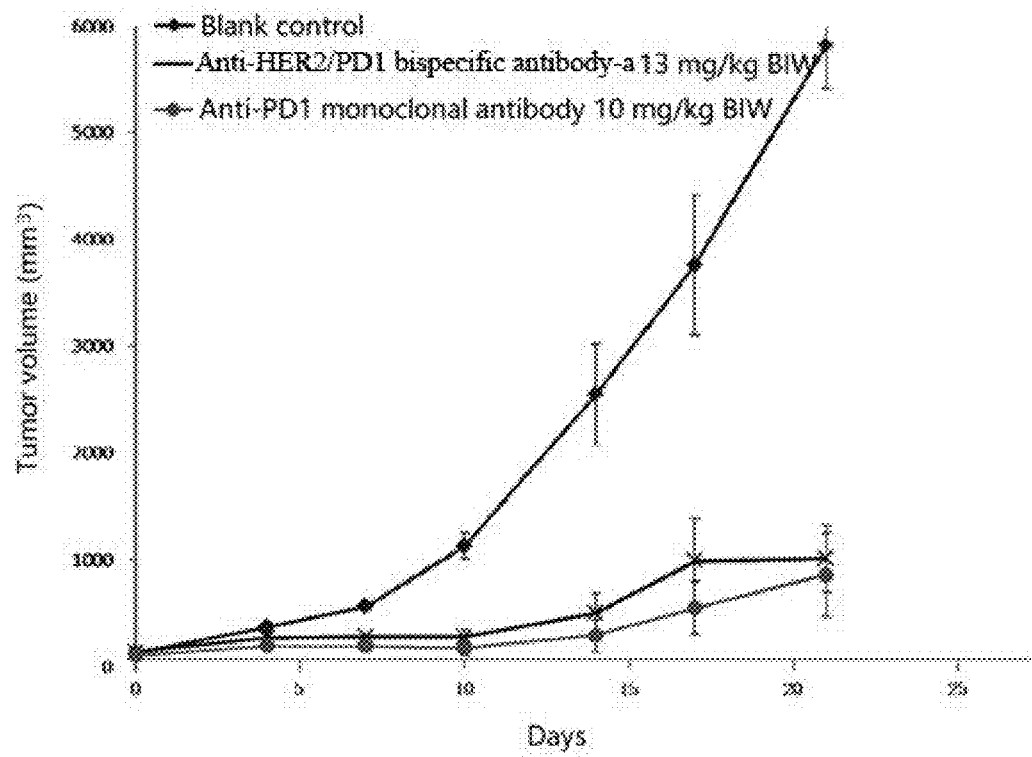
FIG. 11: Anti-tumor effect of anti-HER2/PD1 bispecific antibody-a on humanized PD1 mouse MC38 xenograft model

Example 12. Anti-Tumor Effect of Anti-HER2/PD1 Bispecific Antibody-a on Humanized PD1 Mouse MC38 Xenograft Model The dose of the tested sample anti-HER2/PD1 bispecific antibody-a was 13 mg/kg, the dose of positive control anti-PD1 monoclonal antibody was set to 10 mg/kg, and the control group was given the same volume of normal saline. MC38 mouse colon cancer cells cultured in vitro were collected, and the cell suspension concentration was adjusted to 1×10⁷ cells/ml. Under aseptic conditions, 100 μl of the cell suspension was inoculated subcutaneously into the right rib of humanized PD1 mice. The diameters of subcutaneous xenografts in the humanized PD1 mice were measured with a vernier caliper, and the animals were randomly divided into groups after the average tumor volume grew to 100-200 mm³. Anti-PD1 monoclonal antibody and anti-HER2/PD1 bispecific antibody-a were administered according to the dose, and the control group was given the same amount of normal saline, injected intraperitoneally twice a week for 3 consecutive weeks. During the experiment, the diameters of the xenografts were measured twice a week, and the mice were weighed at the same time. Tumor volume (TV) was calculated by the formula: TV=½× length×width². Relative tumor volume (RTV) was calculated according to the measurement results by the calculation formula: RTV=Vt/V0. Wherein V0 is the tumor volume measured at the beginning of the administration (i.e., d0), and Vt is the tumor volume measured at each time. The evaluation index of anti-tumor activity is the relative tumor proliferation rate T/C (%), which is calculated by the formula as follows: T/C (%)=(TRTV/CRTV)×100 (TRTV: treatment group RTV; CRTV: negative control group RTV). Evaluation standard for efficacy: it is ineffective if T/C (%)>40%; it is effective if T/C (%)≤40% and p≤0.05 by statistics analysis. The experiment was repeated twice. The experimental results are shown in FIG. 11. The results indicate that in the humanized PD1 mouse MC38 xenograft model, anti-HER2/PD1 bispecific antibody-a can inhibit tumor growth by blockading PD1, and the tumor inhibitory effect is similar to that of positive control anti-PD1 monoclonal antibody.

Example 13. Study on the Stability of Anti-HER2/PD1 Bispecific Antibody-a and Anti-HER2/PD1 Bispecific Antibody-b This experiment can be used to evaluate the thermodynamic parameters related to the interaction, such as the unfolding of the protein when the excipients are added, so as to reveal the important mechanism information needed to develop the optimal preparation.

MicroCal VP-Capillary DSC was used in the experiment. The sample and its buffer were filtered with a 0.22 um filter membrane. 400 μl of the sample and its matching buffer were placed in a 96-well plate, respectively. The sample was scanned at 25° C.-100° C., scanning rate was 120° C. per hour.

Figure 12A:
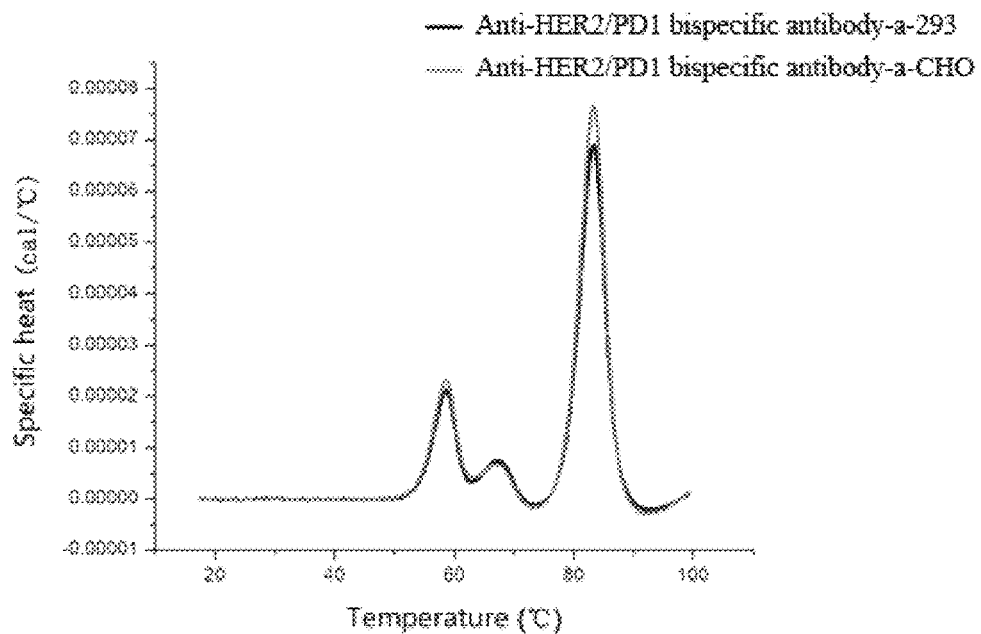
FIG. 12A: DSC pattern of anti-HER2/PD1 bispecific antibody-a
Figure 12B:
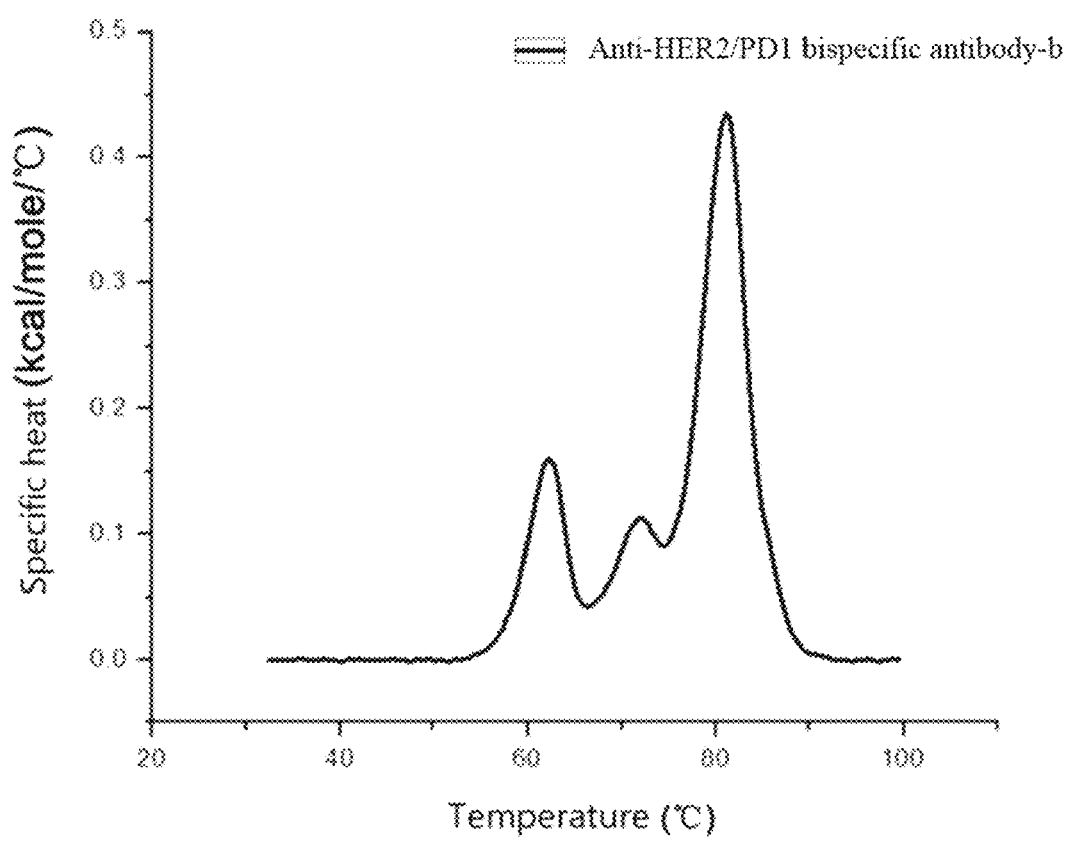
FIG. 12B: DSC pattern of anti-HER2/PD1 bispecific antibody-b
Figure 12C:
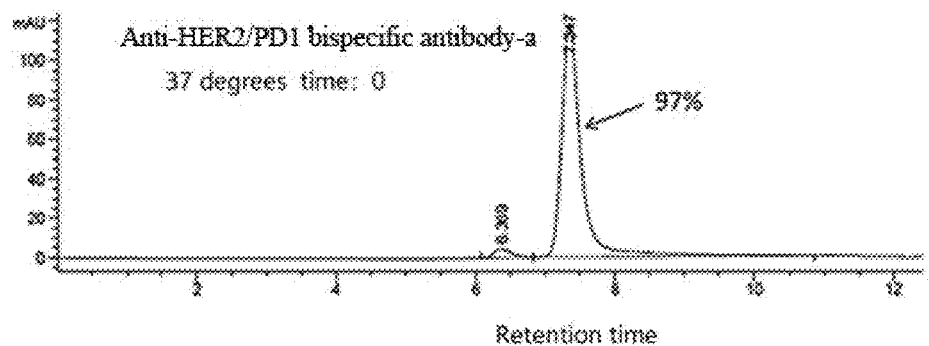
FIG. 12C: Stability at 37° C., SEC-HPLC at day 0 and day 24 of anti-HER2/PD1 bispecific antibody-a
Figure 12C:
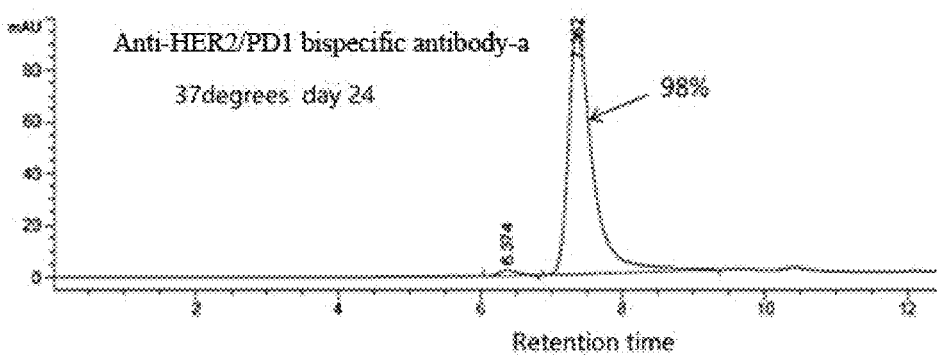
Figure 12D:
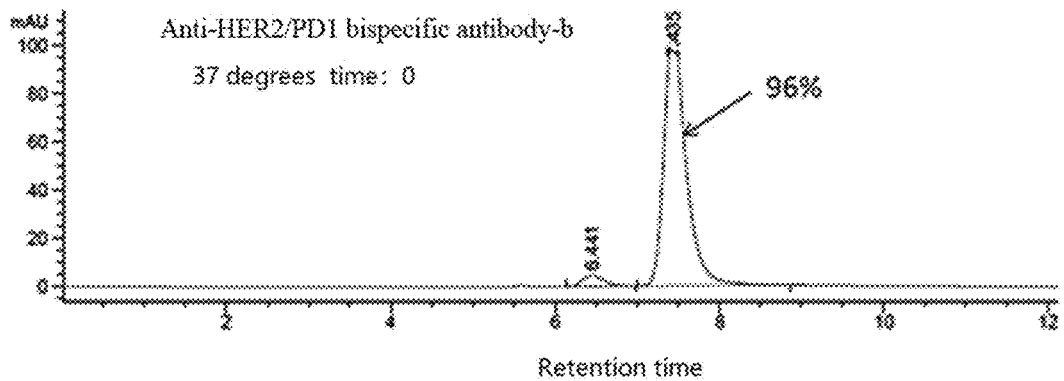
FIG. 12D: Stability at 37° C., SEC-HPLC at day 0 and day 24 of anti-HER2/PD1 bispecific antibody-b
Figure 12D:
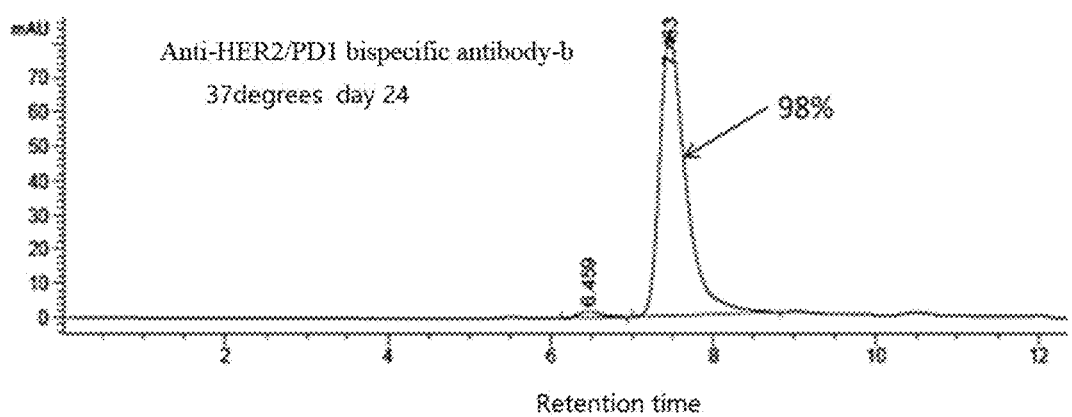

Anti-HER2/PD1 bispecific antibody-a and anti-HER2/PD1 bispecific antibody-b were stored in PBS at pH 7.4. The Tm values of the bispecific antibodies detected by DSC are shown in Table 11. The patterns are shown in FIGS. 12A and 12B. It can be seen that the bispecific antibodies are relatively stable. The results of subsequent long-term stability experiments at 37° C. also verified this. The HPLC-SEC results are shown in FIGS. 12C and 12D.

TABLE 11

| Sample No. | Tm Onset | Tm1 | Tm2 |
|---|---|---|---|
| Anti-HER2/PD1 bispecific antibody-a-CHO | 50 | 58 | 83 |
| Anti-HER2/PD1 bispecific antibody-a-293E | 51 | 58 | 83 |
| Anti-HER2/PD1 bispecific antibody-b-293E | 53 | 62 | 81 |

It can be seen from the above experiments that the bispecific antibodies provided by the present invention have a stable structure. They can bind both HER2 and PD1 antigens at the same time; block the HER2 signaling pathway and can inhibit the proliferation of tumor cells expressing HER2 antigen; can also blockade the PD-1/PD-L1 pathway and restore the immune killing function of T cells and play a role in killing tumor cells. Meanwhile, the anti-HER2/PD1 exhibited strong ADCC towards BT474 tumor cells, comparable to that of anti-HER2 antibody. By contrast, no ADCC towards T cells could be detected.

What is claimed is:

1. A bispecific antibody capable of specifically binding to HER2 and PD1, comprising:
   (a) an immunoglobulin antibody IgG comprising an IgG heavy chain and an IgG light chain, each comprising an N-terminus and a C-terminus; and
   (b) two identical single-chain variable fragments scFv each comprising an N-terminus and a C-terminus,
   wherein each single-chain variable fragment scFv comprises a heavy chain variable region (VH) and a light chain variable region (VL),
   wherein the VH and the VL are connected by a peptide linker L1, and each of the two identical single-chain variable fragment scFv independently is connected in series to the immunoglobulin antibody IgG by a peptide linker L2,
   wherein the VH of the scFv of the bispecific antibody comprises: a complementarity determining region HCDR1, a complementarity determining region HCDR2, and a complementarity determining region HCDR3,
   wherein the HCDR1 has an amino acid sequence comprising SEQ ID NO:1, the HCDR2 has an amino acid sequence comprising SEQ ID NO: 2, and the HCDR3 has an amino acid sequence comprising SEQ ID NO: 3;
   wherein the VL of the scFv of the bispecific antibody comprises: a complementarity determining region LCDR1, a complementarity determining region LCDR2, and a complementarity determining region LCDR3,
   wherein the LCDR1 has an amino acid sequence comprising SEQ ID NO: 4, the LCDR2 has an amino acid sequence comprising SEQ ID NO: 5, and the LCDR3 has an amino acid sequence comprising SEQ ID NO: 6;
   wherein the lgG heavy chain of the immunoglobulin antibody IgG comprises: a complementarity determining region HCDR4, a complementarity determining region HCDR5, and a complementarity determining region HCDR6,
   wherein the HCDR4 has an amino acid sequence comprising SEQ ID NO: 7, the HCDR5 has an amino acid sequence comprising SEQ ID NO: 8, the HCDR6 has an amino acid sequence comprising SEQ ID NO: 9;
   wherein the IgG light chain of the immunoglobulin antibody IgG comprises: a complementarity determining region LCDR4, a complementarity determining region LCDR5, and a complementarity determining region LCDR6,
   wherein LCDR4 has an amino acid sequence comprising SEQ ID NO: 10 LCDR5 has an amino acid sequence comprising SEQ ID NO: 11, LCDR6 has an amino acid sequence comprising SEQ ID NO: 12.

2. The bispecific antibody of claim 1, wherein:
   (a) (i) the VH of the single-chain variable fragment scFv has the amino acid sequence comprising SEQ ID NO: 13, and
   (ii) the VL of the single-chain variable fragment scFv has an amino acid sequence comprising SEQ ID NO:14; and
   (b) (i) the IgG heavy chain has a heavy chain variable region comprising an amino acid sequence comprising SEQ ID NO:15, and
   (ii) the IgG light chain has a light chain variable region comprising an amino acid sequence comprising SEQ ID NO:16.

3. The bispecific antibody of claim 1, wherein the peptide linker L1 has an amino acid sequence comprising SEQ ID NO: 17, and/or the peptide linker L2 has an amino acid comprising SEQ ID NO: 18.

4. The bispecific antibody of claim 1, wherein each of the two identical single-chain variable fragments scFv has a molecular structure of VL-L1-VH, and the N-terminus of each of the two identical single-chain variable fragments scFv is independently connected to the C-terminus of the IgG heavy chain of the immunoglobulin antibody IgG by a peptide linker L2.

5. The bispecific antibody of claim 1, wherein each of the two identical single-chain variable fragments scFv has an amino acid sequence comprising SEQ ID NO: 19.

6. The bispecific antibody of claim 1, wherein:
   (a) the heavy chain of the bispecific antibody has an amino acid sequence comprising SEQ ID NO:20, and
   (b) the light chain of the bispecific antibody has an amino acid sequence of the light chain comprising as shown in SEQ ID NO:21.

7. The bispecific antibody of claim 1, wherein:
   (a) each of the two identical single-chain variable fragments scFv has an molecular structure of VH-L1-VL, and
   (b) the C-terminus of each of the two identical single-chain variable fragments scFv is independently connected to the N-terminus of the IgG heavy chain of the immunoglobulin antibody IgG by a peptide linker L2.

8. The bispecific antibody of claim 1, wherein each of the two identical single-chain variable fragments scFv has an amino acid sequence comprising SEQ ID NO: 24.

9. The bispecific antibody of claim 1, wherein:
(a) the heavy chain of the bispecific antibody has an amino acid sequence comprising SEQ ID NO:25, and
(b) the light chain of the bispecific antibody has an amino acid sequence comprising SEQ ID NO:21.

10. A composition comprising: the bispecific of claim 1; and, one or more pharmaceutically acceptable carriers, diluents or excipients.

* * * * *